(12) United States Patent
Sheffield et al.

(10) Patent No.: US 10,494,634 B2
(45) Date of Patent: Dec. 3, 2019

(54) FACTOR XIA-SPECIFIC APTAMERS

(71) Applicant: CANADIAN BLOOD SERVICES, Ottawa (CA)

(72) Inventors: William Peter Sheffield, Hamilton (CA); David Apraku Donkor, Hamilton (CA)

(73) Assignee: CANADIAN BLOOD SERVICES, Ottawa (CA)

( * ) Notice: Subject to any disclaimer, the term of this patent is extended or adjusted under 35 U.S.C. 154(b) by 0 days.

(21) Appl. No.: 15/586,581

(22) Filed: May 4, 2017

(65) Prior Publication Data

US 2017/0321218 A1     Nov. 9, 2017

Related U.S. Application Data

(60) Provisional application No. 62/331,626, filed on May 4, 2016.

(51) Int. Cl.
| | | |
|---|---|---|
| *C07H 21/04* | (2006.01) | |
| *C12N 15/113* | (2010.01) | |
| *A61K 49/00* | (2006.01) | |
| *G01N 33/86* | (2006.01) | |
| *C12N 15/115* | (2010.01) | |

(52) U.S. Cl.
CPC ...... *C12N 15/1137* (2013.01); *A61K 49/0004* (2013.01); *C12N 15/115* (2013.01); *C12Y 304/21027* (2013.01); *G01N 33/86* (2013.01); *C12N 2310/16* (2013.01); *G01N 2333/96452* (2013.01)

(58) Field of Classification Search
CPC .................................................. C12N 15/111
See application file for complete search history.

(56) References Cited

PUBLICATIONS

Dougan, Hayes, et al. "Evaluation of DNA aptamers directed to thrombin as potential thrombus imaging agents." Nuclear medicine and biology 30.1 (2003): 61-72.*
Al-Horani RA, Desai UR, Factor XIa inhibitors: A review of the patent literature, Expert Opin Ther Pat. 2016;26(3):323-45.
Büller HR, Gailani D, Weitz JI, Factor XI antisense oligonucleotide for venous thrombosis, N Engl J Med. Apr. 23, 2015;372(17):1672.
Extended European Search Report issued in Application No. 17169437.5, dated Oct. 10, 2017.
Müller F, Gailani D, Renné T, Factor XI and XII as antithrombotic targets, Curr Opin Hematol. Sep. 2011;18(5):349-55.
Schumacher WA, Luettgen JM, Quan ML, Seiffert DA, Inhibition of factor XIa as a new approach to anticoagulation, Arterioscler Thromb Vasc Biol. Mar. 2010;30(3):388-92.
Büller et al., *N. Engl. J. Med.* 372.3, 232-240 (2015).
Gysbers et al., *Scientific Reports* 5.11405 (2015).
Navaneetham et al., *The Journal of Biological Chemistry* 280.43, 36165-36175 (2005).
Sheffield et al., *Blood Coagulation and Fibrinolysis* 12, 433-443 (2001).
Tripodi et al., *Clinical Chemistry* 62.5, 699-707 (2016).
Tuerk et al., *Science* 249, 505-510 (1990).

\* cited by examiner

*Primary Examiner* — Kimberly Chong
(74) *Attorney, Agent, or Firm* — Norton Rose Fulbright US LLP

(57) ABSTRACT

The present disclosure concerns aptamers of formula (I) capable of specifically binding to Factor XIa. The aptamers can be used to prevent, treat or alleviate the symptoms of thrombosis. The aptamers can also be used to detect Factor XIa in a sample and/or purify Factor XIa from a sample. The aptamers can further be used to identity putative therapeutic agents for the prevention, treatment or alleviation of symptoms associated with thrombosis.

14 Claims, 12 Drawing Sheets

Specification includes a Sequence Listing.

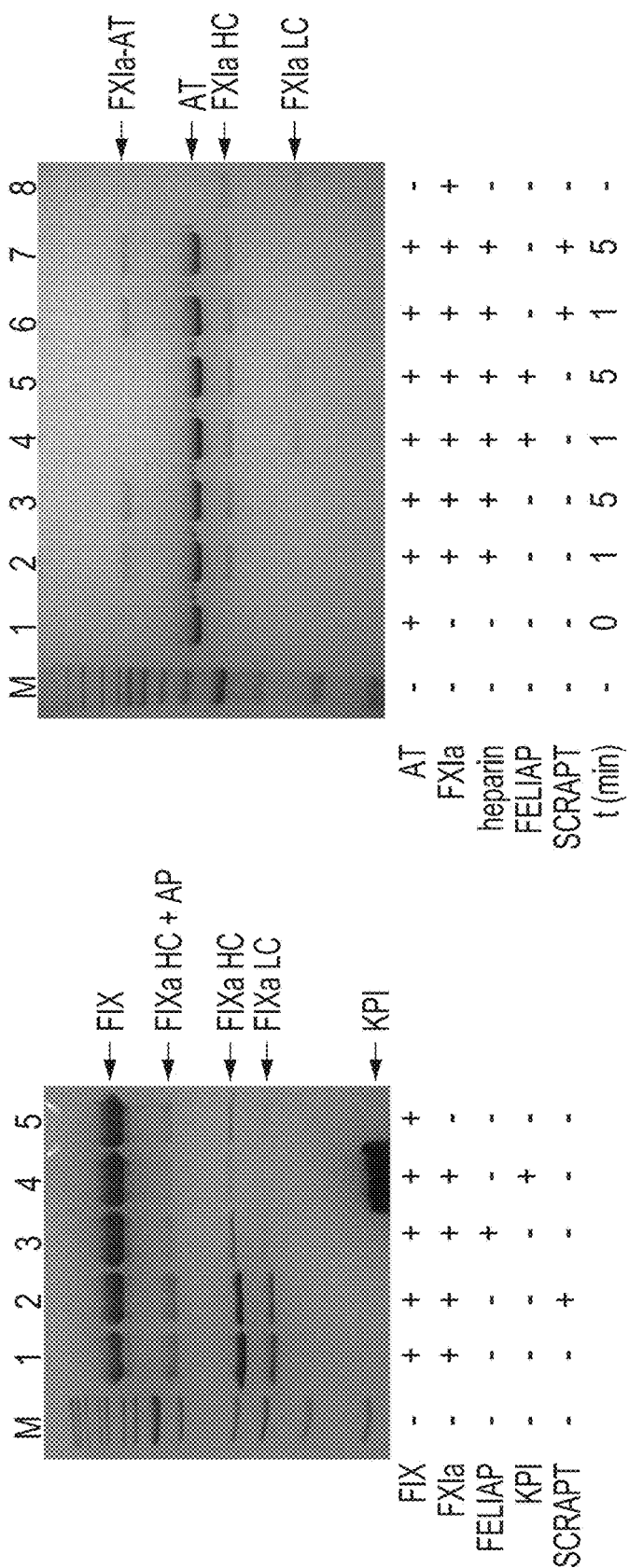

FACTOR XIA-SPECIFIC APTAMERS

CROSS-REFERENCE TO RELATED APPLICATIONS

This application claims priority to U.S. Provisional Application No. 62/331,626 filed May 4, 2016, the entire contents of which disclosure is specifically incorporated herein by reference without disclaimer.

TECHNOLOGICAL FIELD

The present disclosure relates to compounds capable of specifically binding to and limiting the biological activity of Factor XIa.

BACKGROUND

Thromboembolic diseases are a leading cause of morbidity and mortality in the developed world and are rapidly emerging in the developing world. Currently commercialized antithrombotic agents are usually associated with the side effect of causing bleeding. In spite of the introduction of new oral anticoagulants into the clinic in the last few years (e.g., dabigatran etexilate, rivaroxaban, edoxaban for example) there remain unmet needs.

Factor XI inhibition has been identified as an attractive target for drug development because mice or humans with abnormally low FXI levels appear to be protected from thrombosis. An antisense oligonucleotide to FXI named FXI-ASO (ISIS416858) is under clinical development (Büller et al., 2014) and was determined to be superior in preventing venous thromboembolism in patients undergoing total knee replacement than the standard of care. Importantly, the study demonstrated that the antisense oligonucleotide did not promote bleeding in orthopedic surgery, a major challenge with any antithrombic agent. However, it took five weeks for the antisense oligonucleotide FXI-ASO (ISIS416858) to reduce FXI levels by 10 to 20% of normal (e.g. pre-treatment) levels and FXI levels were also slow to recover after the drug was stopped (Buller et al., 2014).

It would be highly desirable to be provided with a specific inhibitor of Factor XIa (FXIa), e.g., a compound which would specifically bind to (and inhibit the biological activity of) Factor XIa. It would also be desirable to be provided with a FXIa inhibitor, which would have a rapid onset of action and/or a short duration of action for treating and/or preventing thrombosis. It would further be highly desirable to be provided with a FXIa inhibitor which would exhibit little to no immunogenicity (upon administration to the intended recipient).

BRIEF SUMMARY

The present disclosure concerns Factor XIa-specific aptamers. The aptamers of the present disclosure are also capable of limiting the biological activity (e.g., the proteolytic activity) of Factor XIa.

In a first aspect, the present disclosure provides an aptamer having the structure of formula (I):

5'-5W-C-3W-3'    (I)

wherein:
"-" refers to a nucleotide bond;
5W has the following first nucleic acid sequence:

(SEQ ID NO: 66)

C has the following second nucleic acid sequence:

(SEQ ID NO: 68)
5'-AACCTATN$_1$N$_2$N$_3$ACTATTN$_4$TN$_5$AN$_6$TN$_7$ATTTTTAN$_8$AN$_9$-3';

3W can be present or absent and when present has the following third nucleic acid sequence:

(SEQ ID NO: 67)
5'-N$_{31}$N$_{32}$N$_{33}$N$_{34}$N$_{35}$N$_{36}$N$_{37}$N$_{38}$N$_{39}$N$_{40}$N$_{41}$-3';

the nucleotides at positions 14 to 18 of SEQ ID NO: 66 are present;

the nucleotides at positions 1 to 33 of SEQ ID NO: 68 are present;

the nucleotides at position 1 to 2 (AA) of SEQ ID NO: 68 are capable of base pairing with nucleotides at position 28 to 27 (TT) of SEQ ID NO: 68;

the nucleotides at position 6 to 8 (ATC) of SEQ ID NO: 68 are capable of base pairing with the nucleotides at position 25 to 23 (TAG) of SEQ ID NO: 68;

the nucleotides at position 11 to 14 (ACTA) of SEQ ID NO: 68 are capable of base pairing with the nucleotides at position 22 to 19 (TN$_6$AN$_5$) of SEQ ID NO: 68; and the nucleotides at position 14 to 18 (N$_{29}$TN$_{30}$TA) of SEQ ID NO: 66 are capable of base pairing with the nucleotides at position 33 to 29 (N$_9$AN$_8$AT) of SEQ ID NO: 68.

In such embodiment, the aptamer can have or consists essentially of the nucleic acid sequence of SEQ ID NO: 64. In still another embodiment, the nucleotides at positions 12 and 13 of SEQ ID NO: 66 and at position 34 and 35 of SEQ ID NO: 68 are present, and the nucleotides at position 12 and 13 (N$_{28}$A) of SEQ ID NO: 66 are capable of base pairing with the nucleotides at position 35 to 34 (N$_{10}$T) of SEQ ID NO: 68. In such embodiment, the aptamer can have or consist essentially of the nucleic acid sequence of SEQ ID NO: 63. In still another embodiment, the nucleotides at position 8 to 11 of SEQ ID NO: 66, at position 1 to 5 of SEQ ID NO: 67 and at position 36 of SEQ ID NO: 68 are present, and the nucleotide at position (N$_{24}$) of SEQ ID NO: 66 is capable of base pairing with the nucleotide a position 2 (N$_{32}$) of SEQ ID NO: 67. In such embodiment, the aptamer of can have or consist essentially of the nucleic acid sequence of SEQ ID NO: 62. In still another embodiment, the nucleotides at position 5 to 7 of SEQ ID NO: 66 and at position 3 to 5 of SEQ ID NO: 67 are present, and the nucleotides at position 6 to 7 (N$_{22}$N$_{23}$) of SEQ ID NO: 66 are capable of base pairing with the nucleotides at positions 4 to 3 (N$_{34}$N$_{33}$) of SEQ ID NO: 67. In such embodiment, the aptamer can have or consist essentially of the nucleic acid sequence of SEQ ID NO: 61. In yet another embodiment, nucleotides 1 to 4 of SEQ ID NO: 66 and nucleotides 6 to 11 of SEQ ID NO: 67 are present. In such embodiment, the aptamer can have or consist essentially of the nucleic acid sequence of SEQ ID NO: 60.

In an second aspect, the present disclosure provides an aptamer having the structure of formula (I) wherein:

5W has the following first nucleic acid sequence:

$$5'-N_{12}N_{13}N_{14}N_{15}N_{16}N_{17}N_{18}N_{19}N_{20}N_{21}N_{22}N_{23}N_{24}N_{71}N_{26}N_{27}N_{28}AN_{29}TN_{30}TA\ 3';$$
(SEQ ID NO: 25)

C has the following second nucleotide sequence:

$$5'-AACCTATN_1N_2N_3ACTATTN_4TN_5AN_6TN_7ATTTTTAN_8AN_9TN_{10}N_{11}-3'.$$
(SEQ ID NO: 23)

3W is present and has the following third nucleotide sequence:

$$5'-N_{31}N_{32}N_{33}N_{34}N_{35}N_{36}N_{37}N_{38}N_{39}N_{40}N_{41}N_{42}N_{43}N_{44}N_{45}-3';$$
(SEQ ID NO: 27)

"-" refers to a nucleotide bond;

the nucleotides at position 1 to 36 of SEQ ID NO: 23, at position 6 to 23 of SEQ ID NO: 25 and at position 1 to 11 of SEQ ID NO: 27 are present;

the nucleotides at position 11 to 13 (ACTA) of SEQ ID NO: 23 are capable of base pairing with the nucleotides at position 22 to 19 ($TN_6AN_5$) of SEQ ID NO: 23;

the nucleotides at position 6 to 8 ($ATN_1$) of SEQ ID NO: 23 are capable of base pairing with the nucleotides at position 25 to 23 ($TAN_7$) of SEQ ID NO: 23;

the nucleotides at position 1 to 2 (AA) of SEQ ID NO: 23 are capable of base pairing with the nucleotides at positions 28 to 27 (TT) of SEQ ID NO: 23;

the nucleotides at position 17 to 23 ($N_{28}AN_{29}TN_{30}T$) of SEQ ID NO: 25 are capable of base pairing with the nucleotides at positions 35 to 27 of SEQ ID NO: 23 ($N_{10}TN_9AN_8A$); and the nucleotides at position 6 to 8 ($N_{22}N_{23}N_{24}$) of SEQ ID NO: 25 are capable of base pairing with the nucleotides at position 4 to 2 ($N_{34}N_{33}N_{32}$) of SEQ ID NO: 27.

In an embodiment, 5W has or consists essentially of the nucleotide sequence of SEQ ID NO: 26. In another embodiment, 3W has of consists essentially of the nucleotide sequence of SEQ ID NO: 28. In still another embodiment, C has or consists essentially of the nucleotide sequence of SEQ ID NO: 24. In yet a further embodiment, the aptamer has or consists essentially of the nucleotide sequence of SEQ ID NO: 1, SEQ ID SEQ ID NO: 6, SEQ ID NO: 8, SEQ ID NO: 9, SEQ ID NO: 10, SEQ ID NO: 11 or SEQ ID NO: 13.

In a third aspect, the present disclosure provides an aptamer having the nucleotide sequence of SEQ ID NO: 2 or SEQ ID NO: 3.

In a fourth aspect, the present disclosure provides a variant of the aptamer described herewith.

In a fifth aspect, the present disclosure provides a fragment of the aptamer described herein.

In a sixth aspect, the present disclosure provides the aptamer described herein, the variant described herein or the fragment described herein for use as a medicament, for example for preventing, treating or alleviating the symptoms of thrombosis. In an embodiment, the aptamer, variant or fragment are for the treatment of initial thrombosis. In another embodiment, the aptamer, variant or fragment are for the prevention of secondary thrombosis.

In a seventh aspect, the present disclosure provides, the aptamer described herein, the variant described herein or the fragment described herein for detecting Factor XIa in a biological sample.

In an eighth aspect, the present disclosure provides a method for detecting Factor XIa in a sample. Broadly, the method comprises (i) contacting the aptamer described herein, the variant described herein or the fragment described herein with the sample; (ii) determining the presence or the absence of a complex between Factor XIa and the aptamer, the variant or the fragment; and (iii) detecting Factor XIa in the sample if the complex of step (ii) is determined to be present. In an embodiment, the method further comprises, when the complex of step (ii) is determined to be present, (iv) quantifying the amount of Factor XIa in the sample based on the amount of the complex.

In a ninth aspect, the present disclosure comprises a method of imaging a clot in a subject. Broadly, the method comprises: (i) administering the aptamer described herein, the variant described herein or the fragment described herein to the subject; (ii) determining the presence or the absence of a complex between Factor XIa and the aptamer, the variant or the fragment; and (iii) imaging a clot in the subject at the location of the complex.

In a tenth aspect, the present disclosure comprises a method of purifying Factor XIa from a sample. Broadly, the method comprises: (i) contacting the aptamer described herein, the variant described herein or the fragment described herein with the sample; (ii) allowing for a complex between Factor XIa and the aptamer, the variant or the fragment to form; and (iii) removing the complex from the sample.

In an eleventh aspect, the present disclosure comprises a method of determining the usefulness of a test agent for the prevention, treatment or the alleviation of symptoms of thrombosis in a subject. Broadly, the method comprises: (i) contacting the test agent with Factor XIa to obtain a test level of the biological activity of Factor XIa, (ii) comparing the test level to a control level of the biological activity of Factor XIa, the control level being derived from or obtained by contacting Factor XIa with the aptamer described herein, the variant described herein or the fragment described herein; and (iii) determining the test agent as being useful for the prevention, treatment or the alleviation of symptoms of thrombosis if the test level is equal to or lower than the control level. In an embodiment, step (i) and/or (ii) further comprises determining the biological activity of Factor XIa by measuring the proteolytic activity of Factor XIa. In another embodiment, step (ii) further comprises providing the aptamer, the variant or the fragment and determining the control level of the biological activity of Factor XIa.

In a twelfth aspect, the present disclosure comprises a method of determining if a test aptamer is useful for the prevention, treatment or the alleviations of symptoms of thrombosis in a subject. Broadly, the method comprises: (i) contacting a test aptamer with Factor XIa to obtain a test level of the biological activity of Factor XIa, (ii) comparing the test level to a control level of the biological activity of Factor XIa, the control level being derived from or obtained by contacting Factor XIa with the aptamer described herein, the variant described herein or the fragment described herein; and (iii) determining the test aptamer as being useful for the prevention, treatment or the alleviation of symptoms of thrombosis if the test level is equal to or lower than the control level. In an embodiment, step (i) and/or (ii) further comprises determining the biological activity of Factor XIa by measuring the proteolytic activity of Factor XIa. In still another embodiment, step (ii) further comprises providing the aptamer, the variant or the fragment and determining the control level of the biological activity of Factor XIa. In still another embodiment, the control level is derived from or obtained by contacting FXIa with a control aptamer having the nucleotide sequence of SEQ ID NO: 1. In yet another embodiment, the test aptamer has at least one nucleotide addition, substitution or deletion when compared to the control aptamer having the nucleotide sequence of SEQ ID NO: 1.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 3A to 3C show the effects of FELIAP on reactions of FXIa and FXI with macromolecular substrates. (A) Coomassie-stained reduced SDS-polyacrylamide gel. FIX was reacted with FXIa in the presence (+) or absence (−) of SCRAPT (lane 2), FELIAP (lane 3) or KPI (lane 4). Arrows and labels, at right, identify the position of FIX, forms of FIXa (including HC, heavy chain, HC+AP, heavy chain+ activation peptide intermediate, LC, light chain) and KPI. M, markers (kDa), at left: 220; 160; 120; 100; 90; 80; 70; 60; 50; 40; 30; 25; 20; 15. (B) As in (A), except antithrombin (AT, lane 1) was reacted with FXIa (lane 8) in the presence of heparin for 1 (lane 2) or 5 (lane 3) minutes with FELIAP (lanes 4 and 5) or SCRAPT (lanes 6 and 7) or no DNA addition (lanes 2 and 3). Arrows and labels identify the position of AT, FXIa-AT covalent complex, FXIa heavy chain (HC) and light chain (LC). M, markers (kDa), at left: 220; 160; 120; 100; 90; 80; 70; 60; 50; 40; 30; 25; 20 (C) As in (A) and (B) except FXI and thrombin (IIa, lane 1) were reacted in the absence (lane 2) or presence of dextran sulphate (DS, lanes 3-7) with the addition of FELIAP (lane 4) or SCRAPT (lane 5) or the thrombin inhibitor hirudin (lane 7). Lane 8, purified FXIa. M, markers (kDa), at left: 220; 160; 120; 100; 90; 80; 70; 60; 50; 40; 30; 25; 20; 15.

DETAILED DESCRIPTION

Figure 1A:
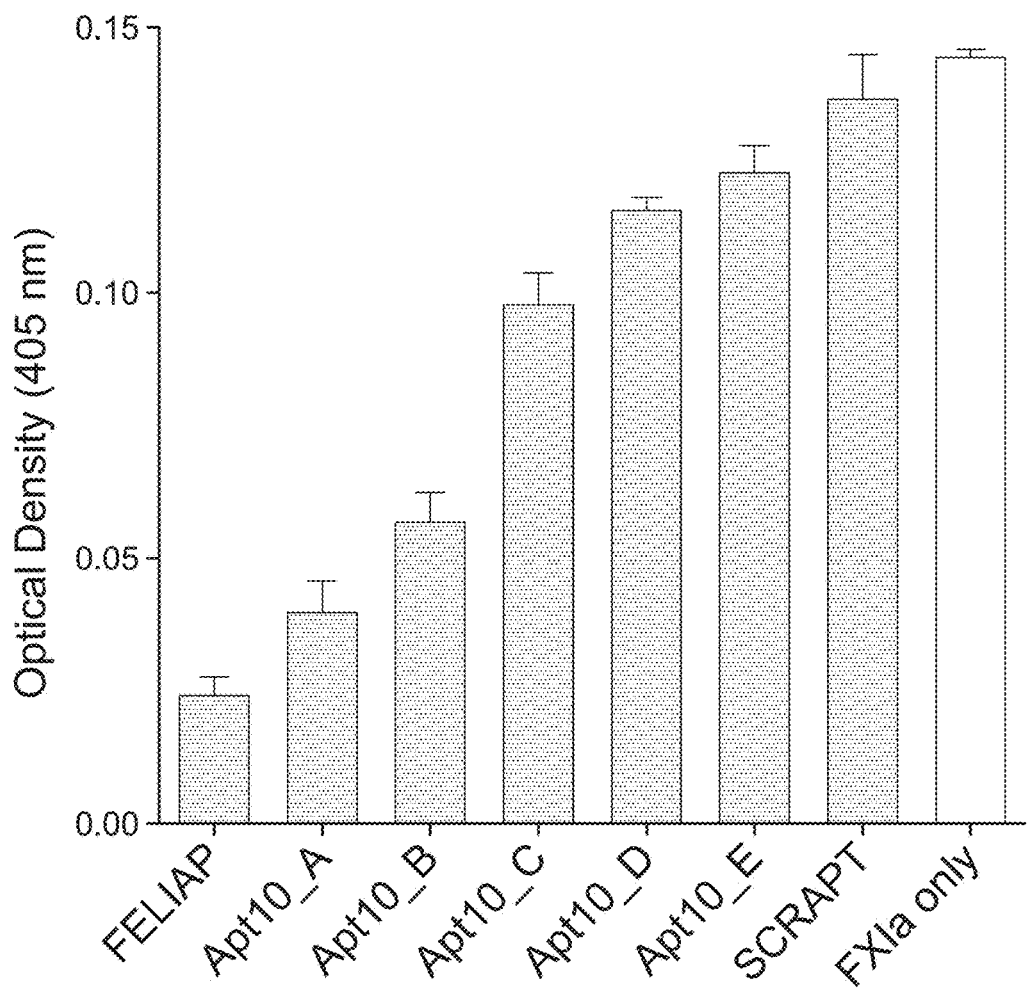
FIGS. 1A and 1B illustrates how aptamers can be used as inhibitors of FXIa-mediated amidolysis. (A) Means±SEM (n=3) of colour generation following FXIa-mediated amidolysis of chromogenic substrate S2366, in the presence (black bars) of Round 10 aptamers identified on the x axis or a scrambled negative control sequence (SCRAPT), or in the absence of added DNA molecules (white bar). (B) Mfold-generated predicted secondary structure of FELIAP. The positions of base substitutions between FELIAP and other Round 10-selected aptamers are indicated by arrows.

In accordance with the present disclosure, there is provided aptamers capable of specifically binding to FXIa. As the aptamers of the present disclosure were obtained using a negative selection with active-site blocked FXIa, they are presumed to specifically bind to the active site of FXIa and, ultimately limit FXIa's biological activity (e.g., proteolytic activity). The aptamers of the present disclosure are defined by their nucleotide sequence as well as their secondary structure. Since FXIa is involved in the onset and maintenance of thrombosis, the aptamers of the present disclosure can be used for preventing, treating or alleviating the symptoms associated with thrombosis. Since the aptamers specifically bind to FXIa, they can also be used to determine the presence or the absence and, optionally the amount, of FXIa in a sample. Further, since the aptamers exhibit inhibitory activity towards FXIa, they can also be used as a control to screen and identify therapeutic agents having improved antithrombotic properties.

Factor XIa-Specific Aptamers

The aptamers of the present disclosure specifically bind to (e.g., are specific for) FXIa. In the context of the present disclosure, the expressions "specific binding" or "specifically bind" refer to the interaction between two elements in a manner that is determinative of the presence of the elements in the presence or absence of a heterogeneous population of molecules. For example, under designated conditions, the aptamers of the present disclosure bind to FXIa and do not bind in a significant manner to other molecules (such as FXI or thrombin for example).

The aptamers of the present disclosure are single-stranded molecules composed of deoxyribonucleic acid (DNA) nucleotides, ribonucleic acid (RNA) nucleotides or a combination of both deoxyribonucleic and ribonucleic acid nucleotides. In an embodiment, the aptamers of the present disclosure are exclusively made of deoxyribonucleic acid (DNA) nucleotides. The aptamers can be composed of naturally-occurring nucleobases (also referred to as bases), sugars and covalent internucleoside (backbone) linkages. The aptamers can also have "non-naturally-occurring" or "synthetic" portions which function similarly. In the context of the present disclosure, the term "nucleotides" refers to a deoxyribonucleic acid nucleotide or to a ribonucleic acid nucleotides.

The aptamers of the present disclosure can include various modifications, e.g., stabilizing modifications, and thus can include at least one modification in the phosphodiester linkage and/or on the sugar, and/or on the base. For example, the aptamer can include one or more phosphorothioate linkages, phosphorodithioate linkages, and/or methylphosphonate linkages. Different chemically compatible modified linkages can be combined, e.g., modifications where the synthesis conditions are chemically compatible. While modified linkages are useful, the aptamer can include phosphodiester linkages, e.g., include at least one phosphodiester linkage, or at least 5%, 10%, 20%, 30% or more phosphodiester linkages. Additional useful modifications include, without restriction, modifications at the 2'-position of the sugar (such as 2'-O-alkyl modifications, 2'-O-methyl modifications, 2'-amino modifications, 2'-halo modifications (e.g., 2'-fluoro) as well as acyclic nucleotide analogs. In another embodiment, the aptamer has modified linkages throughout, e.g., phosphorothioate; has a 3'- and/or 5'-cap; includes a terminal 3'-5' linkage.

In some embodiments, the aptamer includes a concatemer and comprises two or more oligonucleotide sequences joined by one or more linker. The linker may, for example, consist of modified nucleotides or non-nucleotide units. In some embodiments, the linker can provide flexibility to the aptamer. The use of concatemers as aptamers can provide a facile method to synthesize a final molecule, by joining smaller oligonucleotides building blocks to obtain the desired length. For example, a 12 carbon linker ($C_{12}$ phosphoramidite) can be used to join two or more concatemers and provide length, stability and flexibility.

The aptamers of the present disclosure can include a natural or a non-natural backbone. Non-natural or synthetic backbones include, for example, phosphorothioates, chiral phosphorothioates, phosphorodithioates, phosphotriesters aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, carboranyl phosphate and borano-phosphates having normal 3'-5' linkages, 2'-5' linked analogs of these, and those having inverted polarity wherein one or more internucleotide linkages is a 3' to 3', 5' to 5' or 2' to 2' linkage. Aptamers having inverted polarity typically include a single 3' to 3' linkage at the 3'-most internucleotide linkage i.e. a single inverted nucleoside residue which may be abasic (the nucleobase is missing or has a hydroxyl group in place thereof). Some exemplary modified aptamers' backbones that do not include a phosphodiester linkage have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Particularly advantageous are backbone linkages that include one or more charged moieties.

The aptamers of the present disclosure may also contain one or more substituted sugar moieties. For example, such oligonucleotides can include one of the following 2'-modifications: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl, or 2'-O—(O-carboran-1-yl)methyl. Particular examples are $O[(CH_2)_nO]_mCH_3$, $O(CH_2)_n$–$OCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to 10. Other exemplary aptamers can include one of the following 2'-modifications: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl.

Other modifications to the aptamers include Locked Nucleic Acids (LNAs) in which the 2'-hydroxyl group is linked to the 3' or 4' carbon atom of the sugar ring thereby forming a bicyclic sugar moiety. Other modifications include 2'-methoxy (2'-O—$CH_3$), 2'-methoxyethyl (2'O—$CH_2$—$CH_3$), 2'-ethyl, 2'-ethoxy, 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F).

The 2'-modification may be in the arabino (up) position or ribo (down) position. Similar modifications may also be made at other positions on the aptamers, particularly the 3' position of the sugar on the 3' terminal nucleotide or in 2'-5' linked oligonucleotides and the 5' position of the 5' terminal nucleotide. The aptamers may also have sugar mimetics such as cyclobutyl moieties in place of the pentofuranosyl sugar.

The aptamers of the present disclosure can include "unmodified" or "natural" bases (nucleobases) such as adenine (A) and guanine (G), and the pyrimidine bases thymine (T), cytosine (C) and uracil (U). The aptamers may also include base modifications or substitutions. Modified bases include, but are not limited to other synthetic and naturally-occurring bases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—H$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified bases may also include those in which the purine or pyrimidine base is replaced with other heterocycles, for example 7-deaza-adenine, 7-deazaguanosine, 2-aminopyridine and 2-pyridone.

Another type of modification that can be included in the aptamers of the present disclosure are phosphorodithioate linkages. The aptamers comprising modified oligonucleotides containing phosphorothioate or dithioate linkages may also contain one or more substituted sugar moieties particularly modifications at the sugar moieties including, without restriction, 2'-ethyl, 2'-ethoxy, 2'-methoxy, 2'-aminopropoxy, 2'-allyl, 2'-fluoro, 2'-pentyl, 2'-propyl, 2'-dimethylaminooxyethoxy, and 2'-dimethylaminoethoxyethoxy. The 2'-modification may be in the arabino (up) position or ribo (down) position. A preferred 2'-arabino modification is 2'-fluoro. Similar modifications may also be made at other positions on the aptamer, particularly the 3' position of the sugar on the 3' terminal nucleotide or in 2'-5' linked oligonucleotides and the 5' position of 5' terminal nucleotide.

Figure 1B:
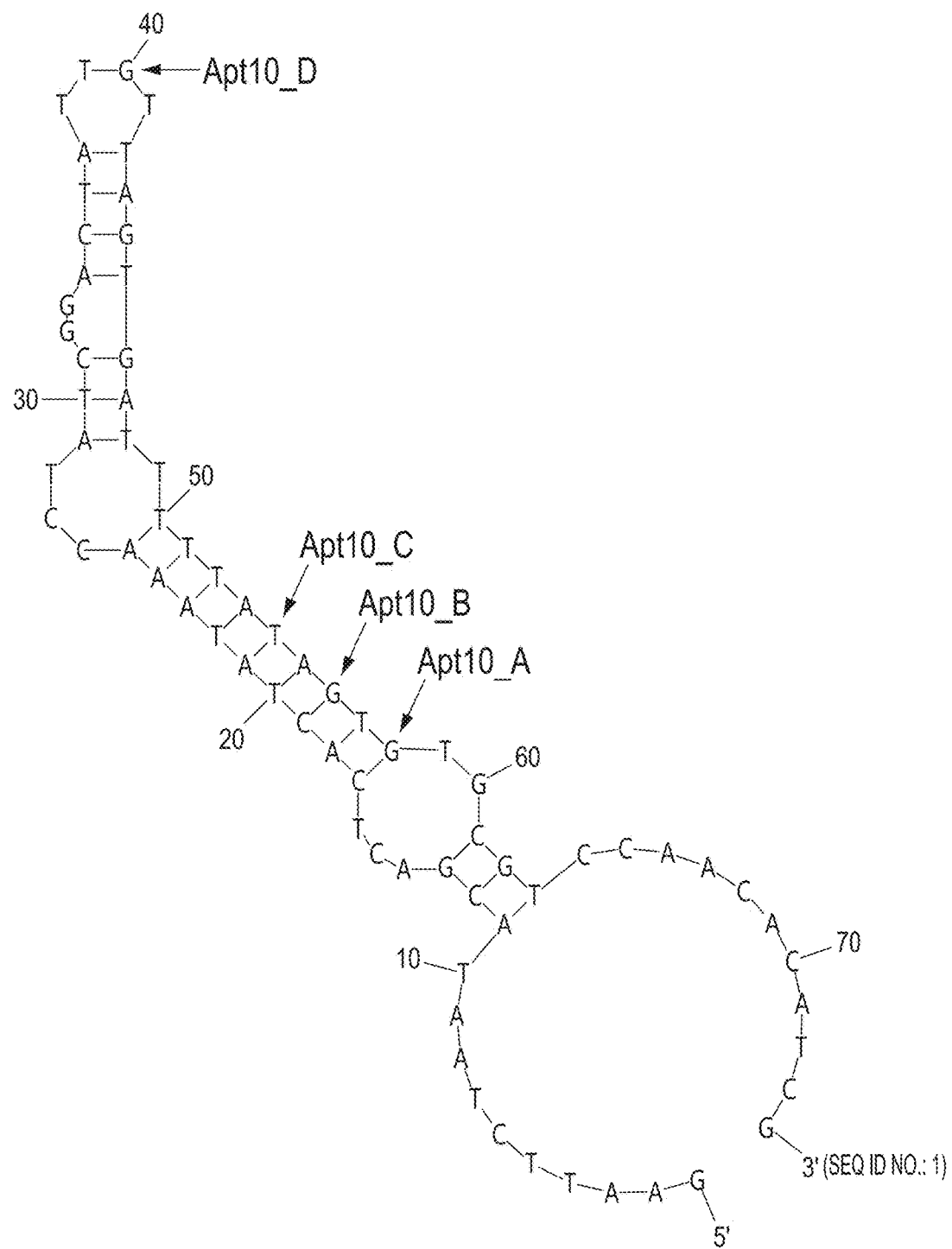

Even though the aptamers of the present disclosure are synthesized as single-stranded molecules they can, under the appropriate conditions (e.g., salt, pH, temperature), form a secondary "hairpin" structure. As shown in FIG. 1B, the aptamer FELIAP forms a hairpin structure in which some stretches of the molecule are capable of base-pairing (e.g., capable of forming sections of double-stranded DNA and/or RNA) with other stretches of the molecule which are located several nucleotides upstream or downstream. As also shown in FIG. 1B, the double-stranded configuration of FELIAP is not observed on the entire length of the molecule, but only in some regions. The aptamers of the present disclosure (which include FELIAP) are also capable of forming a secondary "hairpin" structure which is substantially similar to the one shown on FIG. 1B. The aptamer of the present disclosure forms a hairpin structure in which some stretches of the molecule are capable of base-pairing (e.g., capable of forming sections of double-stranded DNA and/or RNA) with other stretches of the molecule which may be located several nucleotides upstream or downstream. The double-stranded configuration of the aptamer of the present disclosure is not observed on the entire length of the molecule, but only in some regions.

The aptamers of the present disclosure can form at least one stretch (and in an embodiment a combination of stretches) of double stranded DNA and/or RNA between at the following positions:

the nucleotides at position 1 to 2 (AA) of SEQ ID NO: 68 with the nucleotides at position 28 to 27 (TT) of SEQ ID NO: 68;

the nucleotides at position 6 to 8 (ATC) of SEQ ID NO: 68 with the nucleotides at position 25 to 23 (TAG) of SEQ ID NO: 68;

the nucleotides at position 11 to 14 (ACTA) of SEQ ID NO: 68 with the nucleotides at position 22 to 19 (TN$_6$AN$_5$) of SEQ ID NO: 68;

the nucleotides at position 14 to 18 (N$_{29}$TN$_{30}$TA) of SEQ ID NO: 66 with the nucleotides at position 33 to 29 (N$_9$AN$_8$AT) of SEQ ID NO: 68;

the nucleotides at position 12 and 13 (N$_{28}$A) of SEQ ID NO: 66 with the nucleotides at position 35 to 34 (N$_{10}$T) of SEQ ID NO: 68;

the nucleotide at position (N$_{24}$) of SEQ ID NO: 66 with the nucleotide a position 2 (N$_{32}$) of SEQ ID NO: 67;

the nucleotides at position 6 to 7 (N$_{22}$N$_{23}$) of SEQ ID NO: 66 with the nucleotides at positions 4 to 3 (N$_{34}$N$_{33}$) of SEQ ID NO: 67;

the nucleotides at position 11 to 13 (ACTA) of SEQ ID NO: 23 with the nucleotides at position 22 to 19 (TN$_6$AN$_5$) of SEQ ID NO: 23;

the nucleotides at position 6 to 8 (ATN$_1$) of SEQ ID NO: 23 with the nucleotides at position 25 to 23 (TAN$_7$) of SEQ ID NO: 23;

the nucleotides at position 1 to 2 (AA) of SEQ ID NO: 23 with the nucleotides at positions 28 to 27 (TT) of SEQ ID NO: 23;

the nucleotides at position 17 to 23 (N$_{28}$AN$_{29}$TN$_{30}$T) of SEQ ID NO: 25 with the nucleotides at positions 35 to 27 of SEQ ID NO: 23 (N$_{10}$TN$_9$AN$_8$A); and/or the nucleotides at position 6 to 8 (N$_{22}$N$_{23}$N$_{24}$) of SEQ ID NO: 25 with the nucleotides at position 4 to 2 (N$_{34}$N$_{33}$N$_{32}$) of SEQ ID NO: 27.

In the context of the present disclosure, the nucleotides which are not considered capable of base pairing with another nucleotide can form a bulge structure and only form (covalent) bonds with adjacent nucleotides.

The aptamers of the present disclosure include more than contiguous 36 nucleotides. In an embodiment, the aptamers of the present disclosure include at least 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77 or 78 contiguous nucleotides. In still another embodiment, the aptamers of the present disclosure comprise any range of nucleotides between 37 and 78 nucleotides contiguous nucleotides. In yet a further embodiment, the aptamers of the present disclosure have 78 contiguous nucleotides.

The aptamers of the present disclosure have the structure of formula (I):

$$5W\text{-}C\text{-}3W \qquad\qquad (I).$$

The structure of formula (I) comprises three main sections: a 5' wing (referred to as "5W" in formula (I)), a core (referred to as "C" in formula (I)) and an optional 3' wing (referred to as "3W" in formula (I)). The 3' end of the 5W section is associated (e.g., "-" which can be a covalent bond such as, for example, a nucleotide bond, a 5' to 3' nucleotide bond for example) to the 5' end of the C section of the aptamers of the present disclosure. The 3' end of the C section is associated (e.g., "-" which can be a covalent bond such as, for example, a nucleotide bond, a 5' to 3' nucleotide bond for example) to the 5' end of the 3W section of the aptamers of the present disclosure. In some embodiments, the 3W section of the aptamers is absent.

The aptamers of the present disclosure are defined both by their nucleotide sequence and their secondary structure. For example, some of the nucleotides of formula (I) are described of being capable of base pairing with another nucleotide. In the context of the present disclosure, a nucleotide is considered as "being capable of base pairing" with another nucleotide when they can form Watson-Crick base pairing. In such embodiment, C is considered of being capable of base pairing with G, G is considered of being capable of base pairing with C, A is considered of being capable of base pairing with T or U and T or U are considered of being capable of base pairing with A. Other nucleotides of formula (I) are described as not being able to base pair with another nucleotide. Still in the context of the present disclosure, a nucleotide is considered of "not being able to base pair" with another nucleotide when they cannot form Watson-Crick base pairing. For example, C is not able of base pairing with C, A, T or U, G is not able of base pairing with G, A, T or U, A is not able of base pairing with A, C or G, T is not able of base pairing with C, G, T or U and U is not able of base pairing with C, G, T or U.

The core (C) section of the aptamers formula (I) has the following generic nucleotide sequence (IIa) of (IIb):

```
                                   (IIa - SEQ ID NO: 23)
5'-AACCTATN₁N₂N₃ACTATTN₄TN₅AN₆TN₇ATTTTTAN₈AN₉TN₁₀
N₁₁-3'
or
                                   (IIb - SEQ ID NO: 68)
5'-AACCTATN₁N₂N₃ACTATTN₄TN₅AN₆TN₇ATTTTTAN₈AN₉-3'
```

The core section of the aptamers of the present disclosure have nucleotides $N_1$ to $N_{11}$ which are each generic with respect to the identity of the nucleotide base. The aptamers of the present disclosure include all combinations (e.g., generic and specific) of $N_1$ to $N_{11}$ described herewith:

$N_1$ is located at position 8 of SEQ ID NO: 23 and 68 and is any nucleotide (e.g., C, G, A, T/U), provided that it is capable of base-pairing with $N_7$ (e.g., when $N_1$ is C, $N_7$ is G; when $N_1$ is G, $N_7$ is C; when $N_1$ is A, $N_7$ is T or U; when $N_1$ is T or U, $N_7$ is A). In an example, $N_1$ is V (e.g., not T/U). In yet another example, $N_1$ can be A, C or G. In still another example, $N_1$ can be C.

$N_2$ is located at position 9 of SEQ ID NO: 23 and 68 and is any nucleotide (e.g., A, T/U, C or G). In an embodiment, $N_2$ can be K (e.g., G or T/U). In still another embodiment, $N_2$ can be G.

$N_3$ is located at position 10 of SEQ ID NO: 23 and 68 and is any nucleotide (e.g., A, T/U, C or G). For example, $N_3$ can be K (e.g., G or T/U). In another example, $N_3$ can be G.

$N_4$ is located at position 17 of SEQ ID NO: 23 and 68 and is V (e.g., not T/U). For example, $N_4$ can be A, C or G. In yet another example, $N_4$ can be G.

$N_5$ is located at position 19 of SEQ ID NO: 23 and 68 and is D (e.g., not C). For example, $N_5$ can be A, G or T/U. In some embodiments, $N_5$ can be T/U, such as, for example, T.

$N_6$ is located at position 21 of SEQ ID NO: 23 and 68 and is any nucleotide (e.g., A, T/U, C or G). In an embodiment, $N_6$ can be K (e.g., G or T/U). In yet another embodiment, $N_6$ can be G.

$N_7$ is located at position 23 of SEQ ID NO: 23 and 68 and is any nucleotide (e.g., A, T/U, C or G), provided that it is capable of base pairing with $N_1$ (e.g., when $N_7$ is C, $N_1$ is G; when $N_7$ is G, $N_1$ is C; when $N_7$ is A, $N_1$ is T or U; when $N_7$ is T or U, $N_1$ is A). In an embodiment, $N_7$ can be V (e.g., not T/U). In an embodiment, $N_7$ can be A, C or G. For example, $N_7$ can be G.

$N_8$ is located at position 31 of SEQ ID NO: 23 and 68 and is any nucleotide (e.g., A, T/U, C or G), provided that it is capable of base pairing with $N_{30}$ of SEQ ID NO: 25 or 66 (e.g., when $N_8$ is C, $N_{30}$ is G; when $N_8$ is G, $N_{30}$ is C; when $N_8$ is A, $N_{30}$ is T or U; when $N_8$ is T or U, $N_{30}$ is A). For example, $N_8$ can be K (e.g., G or T/U). In yet another example, $N_8$ can be T/U, such as, for example, T.

$N_9$ is located at position 33 of SEQ ID NO: 23 and 68 and is any nucleotide (e.g., A, T/U, C or G), provided that it is capable of base pairing with $N_{29}$ of SEQ ID NO: 25 or 66 (e.g., when $N_9$ is C, $N_{29}$ is G; when $N_9$ is G, $N_{29}$ is C; when $N_9$ is A, $N_{29}$ is T or U; when $N_9$ is T or U, $N_{29}$ is A). In an embodiment, $N_9$ can be K (e.g., G or T/U). In still another embodiment, $N_9$ can be G.

$N_{10}$ is located at position 35 of SEQ ID NO: 23 and is any nucleotide (e.g., A, T/U, C or G), provided that it is capable of base pairing with $N_{28}$ of SEQ ID NO: 25 or 66 (e.g., when $N_{10}$ is C, $N_{28}$ is G; when $N_{10}$ is G, $N_{28}$ is C; when $N_{10}$ is A, $N_{28}$ is T or U; when $N_{10}$ is T or U, $N_{28}$ is A). For example, $N_{10}$ can be K (e.g., G or T/U). In still another example, $N_{10}$ can be G.

$N_{11}$ is located at position 36 of SEQ ID NO: 23. $N_{11}$ can be present or absent. When present, $N_{11}$ can be any nucleotide (e.g., A, T/U, C or G). In an embodiment, $N_u$ can be present. In still yet another example, $N_{11}$ can be T.

A comparison of the core sections of some of the aptamers of the Example is presented in Table 1. In an embodiment, the core region of the aptamers of the present disclosure comprises or consists essentially of any one of the nucleotide sequence of SEQ ID NO: 24, 30 to 35 and 69. In yet another embodiment, the core region of the aptamers of the present disclosure comprises or consists essentially of any one of the nucleotide sequence of SEQ ID NO: 24, 30, 32, 35, 36 and 69. In still another embodiment, the core region of the aptamers of the present disclosure can include or consist essentially of the nucleotide sequence of SEQ ID NO: 24.

TABLE 1

Comparison of the variable domains (core) of some of the aptamers of the Example (see Table 2 for a complete description of the nucleotide sequence of the aptamers). The FELIAP (SEQ ID NO: 1), APT10_A (SEQ ID NO: 9), APT10_B (SEQ ID NO: 13), APT10_C (SEQ ID NO: 14), APT10_D (SEQ ID NO: 6) and APT10_E (SEQ ID NO: 69, not shown in this table) aptamers exhibits FXIa inhibition. Oligonucleotides maked with ** differ from the FELIAP nucleotide sequence.

| Position | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| FELIAP[A] | A | A | C | C | T | A | T | C | G | G | A | C | T | A | T | T | G | T |
| APT10_D[B] | A | A | C | C | T | A | T | C | G | G | A | C | T | A | T | T | G | T |
| NRMAPT7[C] | A | A | C | C | T | A | T | C | G | T** | A | C | T | A | T | T | G | T |
| APT10_A[D] | A | A | C | C | T | A | T | C | G | G | A | C | T | A | T | T | G | T |

TABLE 1-continued

Comparison of the variable domains (core) of some of the aptamers of the Example (see Table 2 for a complete description of the nucleotide sequence of the aptamers). The FELIAP (SEQ ID NO: 1), APT10_A (SEQ ID NO: 9), APT10_B (SEQ ID NO: 13), APT10_C (SEQ ID NO: 14), APT10_D (SEQ ID NO: 6) and APT10_E (SEQ ID NO: 69, not shown in this table) aptamers exhibits FXIa inhibition. Oligonucleotides maked with ** differ from the FELIAP nucleotide sequence.

| | | | | | | | | | | | | | | | | | |
|---|---|---|---|---|---|---|---|---|---|---|---|---|---|---|---|---|---|
| NRMAPT9[E] | A | A | C | C | T | A | T | C | T** | G | A | C | T | A | T | T | G | T |
| NRMAPT10[F] | A | A | C | C | T | A | T | C | G | G | A | C | T | A | T | T | G | T |
| APT10_B[G] | A | A | C | C | T | A | T | C | G | G | A | C | T | A | T | T | G | T |
| APT10_C[H] | A | A | C | C | T | A | T | C | G | G | A | C | T | A | T | T | T** | T |
| NRMAPT14[I] | A | A | C | C | T | A | T | T** | G | G | A | C | T | A | T | T | G | T |
| NRMAPT16[J] | A | A | C | C | T | A | T | C | G | G | A | C | T | A | T | T | G | T |
| NRMAPT17[K] | A | A | C | C | T | A | T | C | G | G | A | C | T | A | T | T | G | T |

| Position | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| FELIAP[A] | T | A | G | T | G | A | T | T | T | T | T | A | T | A | G | T | G | T |
| APT10_D[B] | T | A | G | T | G | A | T | T | T | T | T | A | G** | A | G | T | G | —** |
| NRMAPT7[C] | T | A | G | T | G | A | T | T | T | T | T | A | T | A | G | T | G | T |
| APT10_A[D] | T | A | G | T | G | A | T | T | T | T | T | A | T | A | G | T | T** | T |
| NRMAPT9[E] | T | A | G | T | G | A | T | T | T | T | T | A | T | A | G | T | G | T |
| NRMAPT10[F] | T | A | T** | T | G | A | T | T | T | T | T | A | T | A | G | T | G | T |
| APT10_B[G] | T | A | G | T | G | A | T | T | T | T | T | A | T | A | T** | T | G | T |
| APT10_C[H] | T | A | G | T | G | A | T | T | T | T | T | A | T | A | G | T | G | T |
| NRMAPT14[I] | T | A | G | T | G | A | T | T | T | T | T | A | T | A | G | T | G | T |
| NRMAPT16[J] | T | A | G | T | T** | A | T | T | T | T | T | A | T | A | G | T | G | T |
| NRMAPT17[K] | C** | A | G | T | G | A | T | T | T | T | T | A | T | A | G | T | G | T |

[A]SEQ ID NO: 24, [B]SEQ ID NO: 30, [C]SEQ ID NO: 31, [D]SEQ ID NO: 32, [E]SEQ ID NO: 33, [F]SEQ ID NO: 34, [G]SEQ ID NO: 35, [H]SEQ ID NO: 36, [I]SEQ ID NO: 37, [J]SEQ ID NO: 38, [K]SEQ ID NO: 39

The 5' wing (5W) section of the aptamers of formula (I) has the following generic nucleotide sequence of Formula (IIIa) or (IIIb):

(IIIa - SEQ ID NO: 25)
5'-$N_{12}N_{13}N_{14}N_{15}N_{16}N_{17}N_{18}N_{19}N_{20}N_{21}N_{22}N_{23}N_{24}N_{25}N_{26}$
$N_{27}N_{28}AN_{29}TN_{30}TA$-3' or (IIIb - SEQ ID NO: 66)
5'-$N_{17}N_{18}N_{19}N_{20}N_{21}N_{22}N_{23}N_{24}N_{25}N_{26}N_{27}N_{28}AN_{29}TN_{30}$
TA-3'

The 5W section of the aptamers of the present disclosure have nucleotides which are each generic with respect to the identity of the nucleotide base. The aptamers of the present disclosure include all combinations (e.g., generic and specific) of the nucleotides described herewith.

In an embodiment, the 5W region can have or consist essentially of the nucleic acid sequence of SEQ ID: 25. The aptamers of the present disclosure include all combinations (e.g., generic and specific) of $N_{12}$ to $N_{30}$ described herewith. In embodiments in which the 5W region has or consists essentially of SEQ ID NO: 25, the following embodiments are contemplated:

$N_{12}$ is located at position 1 of SEQ ID NO: 25 and is any nucleotide (e.g., A, T/U, C or G). In an example, $N_{12}$ can be G.

$N_{13}$ is located at position 2 of SEQ ID NO: 25 and is any nucleotide (e.g., A, T/U, C or G). In an example, $N_{13}$ can be A.

$N_{14}$ is located at position 3 of SEQ ID NO: 25 and is any nucleotide (e.g., A, T/U, C or G). For example, $N_{14}$ can be A.

$N_{15}$ is located at position 4 of SEQ ID NO: 25 and is any nucleotide (e.g., A, T/U, C or G). In an embodiment, $N_{15}$ can be T.

$N_{16}$ is located at position 5 of SEQ ID NO: 25 and is any nucleotide (e.g., A, T/U, C or G). In an example, $N_{16}$ can be T.

$N_{17}$ is located at position 6 of SEQ ID NO: 25 and is any nucleotide (e.g., A, T/U, C or G). For example, $N_{17}$ can be C.

$N_{18}$ is located at position 7 of SEQ ID NO: 25 and is any nucleotide (e.g., A, T/U, C or G). In an embodiment, $N_{18}$ can be T.

$N_{19}$ is located at position 8 of SEQ ID NO: 25 and is any nucleotide (e.g., A, T/U, C or G). For example, $N_{19}$ can be A.

$N_{20}$ is located at position 9 of SEQ ID NO: 25 and is any nucleotide (e.g., A, T/U, C or G). In an embodiment, $N_{20}$ can be A.

$N_{21}$ is located at position 10 of SEQ ID NO: 25 and is any nucleotide (e.g., A, T/U, C or G). For example, $N_{21}$ can be T.

$N_{22}$ is located at position 11 of SEQ ID NO: 25 and is any nucleotide (e.g., A, T/U, C or G), provided that it is capable of base pairing with $N_{34}$ of SEQ ID NO: 27 (e.g., when $N_{22}$ is C, $N_{34}$ is G; when $N_{22}$ is G, $N_{34}$ is C; when $N_{22}$ is A, $N_{34}$ is T or U; when $N_{22}$ is T or U, $N_{34}$ is A). In an embodiment, $N_{22}$ can be A.

$N_{23}$ is located at position 12 of SEQ ID NO: 25 and is any nucleotide (e.g., A, T/U, C or G), provided that it is capable of base pairing with $N_{33}$ of SEQ ID NO: 27 (e.g., when $N_{23}$ is C, $N_{33}$ is G; when $N_{23}$ is G, $N_{33}$ is C; when $N_{23}$ is A, $N_{33}$ is T or U; when $N_{23}$ is T or U, $N_{33}$ is A). For example, $N_{23}$ can be C.

$N_{24}$ is located at position 13 of SEQ ID NO: 25 and is any nucleotide (e.g., A, T/U, C or G), provided that it is capable of base pairing with $N_{32}$ of SEQ ID NO: 27 (e.g., when $N_{24}$ is C, $N_{32}$ is G; when $N_{24}$ is G, $N_{32}$ is C; when $N_{24}$ is A, $N_{32}$ is T or U; when $N_{24}$ is T or U, $N_{32}$ is A). For example, $N_{24}$ can be G.

$N_{25}$ is located at position 14 of SEQ ID NO: 25 and is any nucleotide (e.g., A, T/U, C or G). For example, $N_{25}$ can be A.

$N_{26}$ is located at position 15 of SEQ ID NO: 25 and is any nucleotide (e.g., A, T/U, C or G). For example, $N_{26}$ can be C.

$N_{27}$ is located at position 16 of SEQ ID NO: 25 and is any nucleotide (e.g., A, T/U, C or G). For example $N_{27}$ can be T.

$N_{28}$ is located at position 17 of SEQ ID NO: 25 and is any nucleotide (e.g., A, T/U, C or G), provided that it is capable of base pairing with $N_{10}$ of SEQ ID NO: 23 (e.g., when $N_{28}$ is C, $N_{10}$ is G; when $N_{28}$ is G, $N_{10}$ is C; when $N_{28}$ is A, $N_{10}$ is T or U; when $N_{28}$ is T or U, $N_{10}$ is A). For example, $N_{28}$ can be C.

$N_{29}$ is located at position 19 of SEQ ID NO: 25 and is any nucleotide (e.g., A, T/U, C or G), provided that it is capable of base pairing with $N_9$ of SEQ ID NO: 23 (e.g., when $N_{29}$ is C, $N_9$ is G; when $N_{29}$ is G, $N_9$ is C; when $N_{29}$ is A, $N_9$ is T or U; when $N_{29}$ is T or U, $N_9$ is A). For example, $N_{29}$ can be C.

$N_{30}$ is located at position 21 of SEQ ID NO: 25 and is any nucleotide (e.g., A, T/U, C or G), provided that it is capable of base pairing with $N_8$ of SEQ ID NO: 23 (e.g., when $N_{30}$ is C, $N_8$ is G; when $N_{30}$ is G, $N_8$ is C; when $N_{30}$ is A, $N_8$ is T or U; when $N_{30}$ is T or U, $N_8$ is A). For example, $N_{30}$ can be A.

In another embodiment, the 5W region of the aptamers of the present disclosure include or consist essentially of of the nucleotide sequence of GAATTCTAATACGACTCACTATA (SEQ ID NO: 26).

In an embodiment, the 5W region can be truncated (as provided in the nucleic acid sequence of SEQ ID NO: 66) and each nucleotides can be generic with respect to the identity of the nucleotide base. The aptamers of the present disclosure include all combinations (e.g., generic and specific) of $N_{17}$ to $N_{30}$ described herewith. In embodiments in which the 5W region has or consists essentially of SEQ ID NO: 66, the following embodiments are contemplated:

$N_{17}$ is located at position 1 of SEQ ID NO: 66. It can be present of absent. When present, it can be any nucleotide (e.g., A, T/U, C or G). For example, $N_{17}$ can be C.

$N_{18}$ is located at position 2 of SEQ ID NO: 66. It can be absent when $N_{17}$ is also absent. When present, it can be any nucleotide (e.g., A, T/U, C or G). In an embodiment, $N_{18}$ can be T.

$N_{19}$ is located at position 3 of SEQ ID NO: 66. It can be absent when $N_{17}$ and $N_{18}$ are also absent. It can be any nucleotide (e.g., A, T/U, C or G). For example, $N_{19}$ can be A.

$N_{20}$ is located at position 4 of SEQ ID NO: 66. It can be absent when $N_{17}$, $N_{18}$ and $N_{19}$ are also absent. It can be any nucleotide (e.g., A, T/U, C or G). In an embodiment, $N_{20}$ can be A.

$N_{21}$ is located at position 5 of SEQ ID NO: 66. It can be absent when $N_{17}$, $N_{18}$, $N_{19}$ and $N_{20}$ are also absent. It can be any nucleotide (e.g., A, T/U, C or G). For example, $N_{21}$ can be T.

$N_{22}$ is located at position 6 of SEQ ID NO: 66. It can be absent when $N_{17}$, $N_{18}$, $N_{19}$, $N_{20}$ and $N_{21}$ are also absent. It can be any nucleotide (e.g., A, T/U, C or G), provided that it is capable of base pairing with $N_{34}$ of SEQ ID NO: 67 (e.g., when $N_{22}$ is C, $N_{34}$ is G; when $N_{22}$ is G, $N_{34}$ is C; when $N_{22}$ is A, $N_{34}$ is T or U; when $N_{22}$ is T or U, $N_{34}$ is A). In an embodiment, $N_{22}$ can be A.

$N_{23}$ is located at position 7 of SEQ ID NO: 66. It can be absent when $N_{17}$, $N_{18}$, $N_{19}$, $N_{20}$, $N_{21}$ and $N_{22}$ are also absent. It can be and is any nucleotide (e.g., A, T/U, C or G), provided that it is capable of base pairing with $N_{33}$ of SEQ ID NO: 67 (e.g., when $N_{23}$ is C, $N_{33}$ is G; when $N_{23}$ is G, $N_{33}$ is C; when $N_{23}$ is A, $N_{33}$ is T or U; when $N_{23}$ is T or U, $N_{33}$ is A). For example, $N_{23}$ can be C.

$N_{24}$ is located at position 8 of SEQ ID NO: 66. It can be absent when $N_{17}$, $N_{18}$, $N_{19}$, $N_{20}$, $N_{21}$, $N_{22}$ and $N_{23}$ are also absent. It can be and is any nucleotide nucleotide (e.g., A, T/U, C or G), provided that it is capable of base pairing with $N_{32}$ of SEQ ID NO: 67 (e.g., when $N_{24}$ is C, $N_{32}$ is G; when $N_{24}$ is G, $N_{32}$ is C; when $N_{24}$ is A, $N_{32}$ is T or U; when $N_{24}$ is T or U, $N_{32}$ is A). For example, $N_{24}$ can be G.

$N_{25}$ is located at position 9 of SEQ ID NO: 66. It can be absent when $N_{17}$, $N_{18}$, $N_{19}$, $N_{20}$, $N_{21}$, $N_{22}$, $N_{23}$ and $N_{24}$ are also absent. It can be and is any nucleotide (e.g., A, T/U, C or G). For example, $N_{71}$ can be A.

$N_{26}$ is located at position 10 of SEQ ID NO: 66. It can be absent when $N_{17}$, $N_{18}$, $N_{19}$, $N_{20}$, $N_{21}$, $N_{22}$, $N_{23}$, $N_{24}$ and $N_{25}$ are also absent. It can be any nucleotide (e.g., A, T/U, C or G). For example, $N_{26}$ can be C.

$N_{27}$ is located at position 11 of SEQ ID NO: 66. It can be absent when $N_{17}$, $N_{18}$, $N_{19}$, $N_{20}$, $N_{21}$, $N_{22}$, $N_{23}$, $N_{24}$, $N_{25}$ and $N_{26}$ are also absent. It can be any nucleotide (e.g., A, T/U, C or G). For example $N_{27}$ can be T.

$N_{28}$ is located at position 12 of SEQ ID NO: 66. It can be absent when $N_{17}$, $N_{18}$, $N_{19}$, $N_{20}$, $N_{21}$, $N_{22}$, $N_{23}$, $N_{24}$, $N_{25}$, $N_{26}$ and $N_{27}$ are also absent. It can be any nucleotide (e.g., A, T/U, C or G), provided that it is capable of base pairing with $N_{10}$ of SEQ ID NO: 67 (e.g., when $N_{28}$ is C, $N_{10}$ is G; when $N_{28}$ is G, $N_{10}$ is C; when $N_{28}$ is A, $N_{10}$ is T or U; when $N_{28}$ is T or U, $N_{10}$ is A). For example, $N_{28}$ can be C.

$N_{29}$ is located at position 14 of SEQ ID NO: 66. It can be absent when $N_{17}$, $N_{18}$, $N_{19}$, $N_{20}$, $N_{21}$, $N_{22}$, $N_{23}$, $N_{24}$, $N_{25}$, $N_{26}$, $N_{27}$ and $N_{28}$ are also absent. It can be any nucleotide (e.g., A, T/U, C or G), provided that it is capable of base pairing with $N_9$ of SEQ ID NO: 67 (e.g., when $N_{29}$ is C, $N_9$ is G; when $N_{29}$ is G, $N_9$ is C; when $N_{29}$ is A, $N_9$ is T or U; when $N_{29}$ is T or U, $N_9$ is A). For example, $N_{29}$ can be C.

$N_{30}$ is located at position 16 of SEQ ID NO: 66. It can be absent when $N_{17}$, $N_{18}$, $N_{19}$, $N_{20}$, $N_{21}$, $N_{22}$, $N_{23}$, $N_{24}$, $N_{25}$, $N_{26}$, $N_{27}$, $N_{28}$ and $N_{29}$ are also absent. It can be any nucleotide (e.g., A, T/U, C or G), provided that it is capable of base pairing with $N_8$ of SEQ ID NO: 67 (e.g., when $N_{30}$ is C, $N_8$ is G; when $N_{30}$ is G, $N_8$ is C; when $N_{30}$ is A, $N_8$ is T or U; when $N_{30}$ is T or U, $N_8$ is A). For example, $N_{30}$ can be A.

In embodiments in which the 5W region has the nucleic acid sequence of SEQ ID NO: 66, it is provided that the 5W region can correspond to residues 14 to 18, 12 to 18, 5 to 18 or 1 to 18.

The "3' wing" (3W) section of the aptamers of formula (I) has the following generic nucleotide sequence of Formula (IVa) or (IVb):

(IVa - SEQ ID NO: 27)
5'-$N_{31}N_{32}N_{33}N_{34}N_{35}N_{36}N_{37}N_{38}N_{39}N_{40}N_{41}N_{42}N_{43}N_{44}N_{45}$-3' or (IVb - SEQ ID NO: 67)
5'-$N_{31}N_{32}N_{33}N_{34}N_{35}N_{36}N_{37}N_{38}N_{39}N_{40}N_{41}$-3'

The 3W section of the aptamers of the present disclosure have nucleotides which are each generic with respect to the identity of the nucleotide base. The aptamers of the present disclosure include all combinations (e.g., generic and specific) of the nucleotides described herewith. In embodiments in which the the 3W region has or consists essentially of SEQ ID NO: 27, the following embodiments are contemplated:

- $N_{31}$ is located at position 1 of SEQ ID NO: 27 and is any nucleotide (e.g., A, T/U, C or G). For example, $N_{31}$ can be G.
- $N_{32}$ is located at position 2 of SEQ ID NO: 27 and is any nucleotide (e.g., A, T/U, C or G), provided that it is capable of base pairing with $N_{24}$ of SEQ ID NO: 25 (e.g., when $N_{32}$ is C, $N_{24}$ is G; when $N_{32}$ is G, $N_{24}$ is C; when $N_{32}$ is A, $N_{24}$ is T or U; when $N_{32}$ is T or U, $N_{24}$ is A). For example, $N_{32}$ can be C.
- $N_{33}$ is located at position 3 of SEQ ID NO: 27 and is any nucleotide (e.g., A, T/U, C or G), provided that it is capable of base pairing with $N_{23}$ of SEQ ID NO: 25 (e.g., when $N_{33}$ is C, $N_{23}$ is G; when $N_{33}$ is G, $N_{23}$ is C; when $N_{33}$ is A, $N_{23}$ is T or U; when $N_{33}$ is T or U, $N_{23}$ is A). For example, $N_{33}$ can be G.
- $N_{34}$ is located at position 4 of SEQ ID NO: 27 and is any nucleotide (e.g., A, T/U, C or G), provided that it can base pair with $N_{22}$ of SEQ ID NO: 25 (e.g., when $N_{34}$ is C, $N_{22}$ is G; when $N_{34}$ is G, $N_{22}$ is C; when $N_{34}$ is A, $N_{22}$ is T or U; when $N_{34}$ is T or U, $N_{22}$ is A). For example, $N_{34}$ can be T.
- $N_{35}$ is located at position 5 of SEQ ID NO: 27 and is any nucleotide (e.g., A, T/U, C or G). For example, $N_{35}$ can be C.
- $N_{36}$ is located at position 6 of SEQ ID NO: 27 and is any nucleotide (e.g., A, T/U, C or G). For example, $N_{36}$ can be C.
- $N_{37}$ is located at position 7 of SEQ ID NO: 27 and is any nucleotide (e.g., A, T/U, C or G). For example, $N_{37}$ can be A.
- $N_{38}$ is located at position 8 of SEQ ID NO: 27 and is any nucleotide (e.g., A, T/U, C or G). For example, $N_{38}$ can be A.
- $N_{39}$ is located at position 9 of SEQ ID NO: 27 and is any nucleotide (e.g., A, T/U, C or G). For example, $N_{39}$ can be C.
- $N_{40}$ is located at position 10 of SEQ ID NO: 27 and is any nucleotide (e.g., A, T/U, C or G). For example, $N_{40}$ can be A.
- $N_{41}$ is located at position 11 of SEQ ID NO: 27 and is any nucleotide (e.g., A, T/U, C or G). For example, $N_{41}$ can be C.
- $N_{42}$ is located at position 12 of SEQ ID NO: 27 and is any nucleotide (e.g., A, T/U, C or G). For example, $N_{42}$ can be A.
- $N_{43}$ is located at position 13 of SEQ ID NO: 27 and is any nucleotide (e.g., A, T/U, C or G). For example, $N_{43}$ can be T.
- $N_{44}$ is located at position 14 of SEQ ID NO: 27 and is any nucleotide (e.g., A, T/U, C or G). For example, $N_{44}$ can be C.
- $N_{45}$ is located at position 15 of SEQ ID NO: 27 and is any nucleotide (e.g., A, T/U, C or G). For example, $N_{45}$ can be G.

In an embodiment, the 3W region of the aptamers of the present disclosure include or consist essentially of the nucleotide sequence of GCGTCCAACACATCG (SEQ ID NO: 28).

In an embodiment, the 3W region can be truncated (as provided in the nucleic acid sequence of SEQ ID NO: 67) and each nucleotides can be generic with respect to the identity of the nucleotide base. The aptamers of the present disclosure include all combinations (e.g., generic and specific) of $N_{31}$ to $N_{41}$ described herewith. In embodiments in which the 5W region has or consists essentially of SEQ ID NO: 67, the following embodiments are contemplated:

- $N_{31}$ is located at position 1 of SEQ ID NO: 67. It can be absent if $N_{32}$, $N_{33}$, $N_{34}$, $N_{35}$, $N_{36}$, $N_{37}$, $N_{38}$, $N_{39}$, $N_{40}$ and $N_{41}$ are absent. It can be and is any nucleotide (e.g., A, T/U, C or G). For example, $N_{31}$ can be G.
- $N_{32}$ is located at position 2 of SEQ ID NO: 67. It can be absent if $N_{33}$, $N_{34}$, $N_{35}$, $N_{36}$, $N_{37}$, $N_{38}$, $N_{39}$, $N_{40}$ and $N_{41}$ are absent. It can be any nucleotide (e.g., A, T/U, C or G), provided that it is capable of base pairing with $N_{24}$ of SEQ ID NO: 66 (e.g., when $N_{32}$ is C, $N_{24}$ is G; when $N_{32}$ is G, $N_{24}$ is C; when $N_{32}$ is A, $N_{24}$ is T or U; when $N_{32}$ is T or U, $N_{24}$ is A). For example, $N_{32}$ can be C.
- $N_{33}$ is located at position 3 of SEQ ID NO: 67. It can be absent if $N_{34}$, $N_{35}$, $N_{36}$, $N_{37}$, $N_{38}$, $N_{39}$, $N_{40}$ and $N_{41}$ are absent. It can be any nucleotide (e.g., A, T/U, C or G), provided that it is capable of base pairing with $N_{23}$ of SEQ ID NO: 66 (e.g., when $N_{33}$ is C, $N_{23}$ is G; when $N_{33}$ is G, $N_{23}$ is C; when $N_{33}$ is A, $N_{23}$ is T or U; when $N_{33}$ is T or U, $N_{23}$ is A). For example, $N_{33}$ can be G.
- $N_{34}$ is located at position 4 of SEQ ID NO: 67. It can be absent if $N_{35}$, $N_{36}$, $N_{37}$, $N_{38}$, $N_{39}$, $N_{40}$ and $N_{41}$ are absent. It can be any nucleotide (e.g., A, T/U, C or G), provided that it can base pair with $N_{22}$ of SEQ ID NO: 66 (e.g., when $N_{34}$ is C, $N_{22}$ is G; when $N_{34}$ is G, $N_{22}$ is C; when $N_{34}$ is A, $N_{22}$ is T or U; when $N_{34}$ is T or U, $N_{22}$ is A). For example, $N_{34}$ can be T.
- $N_{35}$ is located at position 5 of SEQ ID NO: 67. It can be absent if $N_{36}$, $N_{37}$, $N_{38}$, $N_{39}$, $N_{40}$ and $N_{41}$ are absent. It can be any nucleotide (e.g., A, T/U, C or G). For example, $N_{35}$ can be C.
- $N_{36}$ is located at position 6 of SEQ ID NO: 67. It can be absent if $N_{37}$, $N_{38}$, $N_{39}$, $N_{40}$ and $N_{41}$ are absent. It can be any nucleotide (e.g., A, T/U, C or G). For example, $N_{36}$ can be C.
- $N_{37}$ is located at position 7 of SEQ ID NO: 67. It can be absent if $N_{38}$, $N_{39}$, $N_{40}$ and $N_{41}$ are absent. It can be any nucleotide (e.g., A, T/U, C or G). For example, $N_{37}$ can be A.
- $N_{38}$ is located at position 8 of SEQ ID NO: 67. It can be absent if $N_{39}$, $N_{40}$ and $N_{41}$ are absent. It can be any nucleotide (e.g., A, T/U, C or G). For example, $N_{38}$ can be A.
- $N_{39}$ is located at position 9 of SEQ ID NO: 67. It can be absent if $N_{40}$ and $N_{41}$ are absent. It can be any nucleotide (e.g., A, T/U, C or G). For example, $N_{39}$ can be C.
- $N_{40}$ is located at position 10 of SEQ ID NO: 67. It can be absent if $N_{41}$ is absent. It can be any nucleotide (e.g., A, T/U, C or G). For example, $N_{40}$ can be A.
- $N_{41}$ is located at position 11 of SEQ ID NO: 67. It can be absent. It can be any nucleotide (e.g., A, T/U, C or G). For example, $N_{41}$ can be C.

In embodiments in which the 3W region has the nucleic acid sequence of SEQ ID NO: 67, it is provided that the 3W region can correspond to residues 1 and 2, 1 to 5 or 1 to 11.

The aptamers of the present disclosure forms a modified "hairpin" structure comprising both regions of double stranded (e.g., Watson-Crick base paired) nucleotides (e.g., stems) and regions of single stranded nucleotides (e.g., bulges). The "stem" regions refer to regions of the aptamers that are capable of base pairing and, under the appropriate conditions, form double stranded regions. Since the aptamers are in an hairpin configuration, the stem regions involve base pairing of a first section in the 5'→3' orientation with a second section in the 3'→5' orientation. The "bulge" regions refer to regions of the aptamers which remain single stranded and, due to the secondary structure of the rest of the aptamers, protrude outward from the stem regions. The aptamers of the present disclosure have at least one stem region and at least one bulge region. In an embodiment, the aptamers of the present disclosure comprise four "stem" regions and five "bulge" regions. In such embodiments, each stem region is flanked (on each side) by a bulge region.

The aptamers of formula (I) can have up to four stem regions (designated herein as a first, a second, a third and a fourth stem region) and the nucleotides which are not located in the stem regions (e.g., the remaining nucleotides) are considered to be located in one of the bulge regions. As such, the nucleotides at position 3 to 5, 9, 10, 15 to 18, 26 and 36 of SEQ ID NO: 23 (as well as the corresponding positions in SEQ ID NO: 68) lack the ability to base pair (e.g., cannot base pair) with any other nucleotides of the aptamers Formula (I) and are in a single stranded configuration. In addition, the nucleotides at position 1 to 10 and 14 to 16 of SEQ ID NO: 25 (as well the corresponding positions in SEQ ID NO: 66) lack the ability to base pair (e.g., cannot base pair) with any other nucleotides of the aptamers Formula (I) and are in a single stranded configuration. Further, the nucleotides at position 1 and 5 to 15 of SEQ ID NO: 27 (as well as the corresponding positions in SEQ ID NO: 67) lack the ability to base pair with any other nucleotides of Formula (I) and are in a single stranded configuration.

The first stem region of the aptamers of Formula (I) involves the base pairing of the nucleotides located at position 11 to 14 of SEQ ID NO: 23 or 68 with the nucleotides located at positions 22 to 19 of SEQ ID NO: 23 or 68. As such, in the aptamers of formula (I), the nucleotides at position 11 to 14 of SEQ ID NO: 23 or 68 are capable of base pairing with nucleotides at position 22 to 19 of SEQ ID NO: 23 or 68.

The first stem region can be flanked by a first bulge region and a second bulge region. The first bulge region can consist of nucleotides located at positions 15 to 18 of SEQ ID NO: 23 or 68. The second bulge region can consist of nucleotides located at positions 9 and 10 of SEQ ID NO: 23 or 68.

The second stem region of the aptamers of Formula (I) involves the base pairing of the nucleotides located at position 6 to 8 of SEQ ID NO: 23 or 68 with the nucleotides located at positions 17 to 23 of SEQ ID NO: 23 or 68. As such, in the aptamers of formula (I), the nucleotides at position 6 to 8 of SEQ ID NO: 23 or 68 are capable of base pairing with the nucleotides at position 17 to 23 of SEQ ID NO: 23 or 68.

The second stem region can be flanked by the second bulge region (described above) and a third bulge region. The third bulge region can consist of nucleotides at positions 2 to 4 and 26 of SEQ ID NO: 23 or 68.

The third stem region of the aptamers of formula (I) involves the base pairing of the nucleotides located at position 17 to 23 of SEQ ID NO: 25 (or position 12 to 18 of SEQ ID NO: 66) and at positions 1 and 2 of SEQ ID NO: 23 or 68 with the nucleotides located at positions 35 to 27 of SEQ ID NO: 23 or 68. As such, in the aptamers of formula (I), the nucleotides at position 19 to 23 of SEQ ID NO: 25 (or position 12 to 18 of SEQ ID NO: 66) and at position 1 and 2 of SEQ ID NO: 23 or 68 are capable of base pairing with the nucleotides at positions 35 to 27 of SEQ ID NO: 23 or 68.

The third stem region can flanked by the third bulge region (as indicated above) and a fourth bulge region. The fourth bulge region can consist of the nucleotides at position of 14 to 16 SEQ ID NO: 25 (or position 9 to 11 of SEQ ID NO: 66), the nucleotide at position 36 of SEQ ID NO: 23 or 68 and the nucleotide at position 1 of SEQ ID NO: 27 or 67.

The fourth stem region of the aptamers of formula (I) involves the base pairing of the nucleotides located at position 11 to 13 of SEQ ID NO: 25 (or position 6 to 8 of SEQ ID NO: 66) with the nucleotides located at positions 4 to 2 of SEQ ID NO: 27 or 67. As such, in the aptamers of formula (I), the nucleotides at position 11 to 13 of SEQ ID NO: 25 (or at position 6 to 8 of SEQ ID NO: 66) are capable of base pairing with the nucleotides at position 4 to 2 of SEQ ID NO: 27 or 67.

The fourth stem regions can be flanked by the fourth bulge region (as indicated above) and a fifth bulge region. The fifth bulge region can consist of the nucleotides at position 1 to 10 of SEQ ID NO: 25 (or position 1 to 6 of SEQ ID NO: 66) and the nucleotides at position 15 to 5 of SEQ ID NO: 27 (or position 11 to 5 of SEQ ID NO: 68).

The present disclosure also provides variants of the aptamers of Formula (I) provided that such variants are capable of specifically binding to FXIa. In some embodiments, the variants of the aptamers of Formula (I) can exhibit some FXIa inhibitory activity. A "variant" of the aptamers of Formula (I) (also referred to as an aptamer variant) has at least one nucleotide addition or substitution when compared to the aptamers of Formula (I). The one or more added or substituted nucleotides that can be located anywhere in the molecule. The level of identity between the variants and the aptamers of Formula (I) is at least 70%, 75%, 80%, 85%, 90%, 95%, 96%, 97%, 98% or 99% over the entire length of the aptamers. In an embodiment, the variant aptamer has one or more of the stem and buldge region as described herein.

The present disclosure further provides fragments of the aptamers of Formula (I) and variants of the aptamers of Formula (I) provided that such fragments retain the ability to specifically bind to FXIa. In some embodiments, the fragments of the aptamers of Formula (I) and of the aptamers of Formula (I) can exhibit some FXIa inhibitory activity. A "fragment" of the aptamers of Formula (I) (also referred to as an aptamer fragment) has at least one less nucleotide than the aptamers of Formula (I) or the variants described herein. The one or more nucleotides that can be removed from the aptamers of Formula (I) to provide the "fragments" can be located anywhere in the molecule. For example, the one or more nucleotide that can be removed from the aptamers of Formula (I) can be located, at the 5' end of the molecule, at the vicinity of the 5' end of the molecule, at the 3' end of the molecule and/or at the vicinity of the 3' end of the molecule. In an embodiment, the fragment is a 5'- and/or a 3'-end truncation of one or more nucleotides. In some embodiments, the fragments of the aptamers of Formula (I) have at least 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 contiguous nucleotides of the aptamers of Formula (I). In an embodiment, the aptamer fragment has one or more of the stem and buldge region as described herein.

Therapeutic Uses of the Factor XIa-Specific Aptamers

The FXIa-specific aptamers are capable of limiting (and in some embodiments, inhibiting) the activation of Factor IX (e.g., the proteolytic cleavage of Factor IX into Factor IXa). The FXIa-specific aptamers are capable of limiting (and in some embodiments, inhibiting) the generation of thrombin in plasma. Since the FXIa-specific aptamers have a rapid onset of action, they can be used in an acute setting to achieve therapeutic effects. In addition, since the FXIa-specific aptamers have a relatively short duration of therapeutic action (when compared to FXI-specific antisense), they provide ease in ending the therapy and limiting unwanted side effects. In some embodiment, the FXIa-specific aptamers of the present disclosure have a short duration of action, e.g. after administration, they exhibit their therapeutic activity during one or more hours, during one or more days, but during less than a week. Consequently, the FXIa-specific aptamers can be used to prevent, treat or alleviate the symptoms of thrombosis (or a thrombotic condition) in a subject in need thereof.

The Factor XIa-specific aptamers disclosed herein can be formulated into a pharmaceutical composition for administration to a subject in need thereof. In an embodiment, the subject is a mammal, such as a human. More specifically, the FXIa-specific aptamers can be admixed with a carrier and formulated in a pharmaceutical composition. As used herein, a carrier or "pharmaceutically acceptable carrier" is a pharmaceutically acceptable solvent, suspending agent or any other pharmacologically inert vehicle for delivering one or more compounds to the subject, and is typically liquid or solid. A pharmaceutical carrier is generally selected to provide the desired property (bulk, consistency, etc.), when combined with components of a given pharmaceutical composition, in view of the intended administration mode.

The FXIa-specific aptamers or the pharmaceutical composition comprising same may be administered in a unit dosage form. Conventional pharmaceutical practice may be employed to provide suitable formulations or compositions to administer such compositions to subjects. Although intravenous administration is preferred, any appropriate route of administration may be employed, for example, oral, parenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. The FXIa aptamers or the pharmaceutical composition may be in the form of a liquid solution or a suspension for intravenous administration, in the form of a tablet or a capsule for oral administration, in the form of a powder, nasal drops, or an aerosol for intranasal formulations.

In order to provide a therapeutic benefit, the FXIa-specific aptamers or the pharmaceutical composition comprising same is administered at a "pharmaceutically/therapeutically effective amount". The expressions "pharmaceutically effective amount" or "therapeutically effective amount" refers to an amount (dose) effective in preventing a condition in a subject, treating a subject and/or alleviating its symptoms. It is also to be understood herein that a "pharmaceutically effective amount" of the FXIa-specific aptamers can be interpreted as an amount giving a desired therapeutic effect, either taken in one dose or in any dosage or route, taken alone or in combination with other therapeutic agents.

When used in therapy and a very specific window of exposure to the FXIa-specific aptamers is warranted (for example to limit the appearance or maintenance of unwanted side effects), it is possible to use a modified FXIa-specific aptamer bearing a biotin group. The biotin group can be located at any position on the aptamer, but is preferably located at or near the 5' or the 3' end of the molecule. The biotin group itself is not intended to reduce or dampen the therapeutic activity of the FXIa-specific aptamer but provides means for removing (inactivating) the aptamer of the present disclosure. In fact, in the presence of avidin, the biotin group is capable of forming a complex which will prevent the FXIa-specific aptamer from mediating its therapeutic activity (e.g., limiting the biological activity of FXIa) by removing it from general circulation. As such, when therapeutic effects of the FXIa-specific aptamers are warranted, no avidin is administered to the treated subject. However, when the therapeutic effects of the FXIa-specific aptamers are no longer warranted, avidin can be administered to the treated subject to reduce the therapeutic activity of the aptamers.

The FXIa-specific aptamers can be used to prevent, treat or alleviation the symptoms of thrombosis (e.g. including initial thrombosis and a secondary thrombosis). The FXIa-specific aptamers can be used as thrombolytic agents, adjunct therapy or as anticoagulants. In some embodiments, the FXIa-specific aptamers can be used to treat an initial thrombosis (e.g., a first diagnosed thrombosis in a subject) and/or prevent a secondary thrombosis (e.g., a subsequent thrombosis in a subject).

In another embodiment, the FXIa-specific aptamers can be used as thrombolytic agents (e.g., indirect thrombolytic agents) for dissolving a clot in vivo. In order to do so, a therapeutic dose of the FXIa-specific aptamers is administered to a subject in need thereof (having one or more clots and would benefit from reducing the size and/or number of the one or more clots). In some embodiments, the FXIa-specific aptamers can be used to treat thrombosis (or a thrombotic-associated condition) in a subject in need thereof. For example, the FXIa-specific aptamers can be used to treat an initial thrombosis (e.g., a first thrombotic event in a subject). In such embodiments, the FXIa-specific aptamers can be used alone, or in combination with another thrombolytic agent.

In another embodiment, the administration of the FXIa-specific aptamers or the pharmaceutical composition comprising same can be used as an adjunct therapy to bolster the effect of a thrombolytic agent. Such agents include, but are not limited to, tPA, a tissue plasminogen activator variant (such as, for example, tenecteplase), urokinase and streptokinase. When used in combination with the FXIa-specific aptamers, it is possible to administer a lower dose of a thrombolytic agent, even a dose to be considered subtherapeutic (when administered in the absence of the FXIa-specific aptamers). In an additional or optional embodiment, when used in combination with a FXIa-specific aptamer, it may be possible to administer the thrombolytic agent at a time which is considered outside the effective window after the onset of symptoms (e.g. more than three hours after myocardial infarction or 5 hours after stroke) and still observe beneficial therapeutic effect in the subject.

In yet another embodiment, the FXIa-specific aptamers are able to reduce the formation of a clot and as such can be used as anticoagulants. In order to do so, a therapeutic dose of the the FXIa-specific aptamers of the pharmaceutical composition comprising same is administered to a subject in need thereof (having a clot(s) and could benefit from reducing the formation of the clot(s)). The FXIa-specific aptamers can be used alone or in combination with another anticoagulant, such as, for example, heparin or its derivatives. For example, the FXIa-specific aptamers can be used to prevent an initial thrombosis (e.g., a first thrombotic event in a subject) in a subject at risk of developing the initial thrombosis (e.g. a subject intended to be surgically operated). In another example, the FXIa-specific aptamers can be used to prevent a secondary thrombosis (e.g., a subsequent thrombotic event in the subject).

Factor XIa-Specific Aptamer Methods

Since the aptamers of the present disclosure are able to specifically bind to Factor XIa, they can be used to either detect the presence of Factor XIa or purify Factor XIa from a mixture comprising other components. In the methods using the aptamers of the present disclosure, a label (either covalently associated or non-covalently associated) is preferably used. In methods of detecting FXIa, the label is preferably a detectable label. In methods of purifying FXIa, the label is an affinity label.

In an embodiment, the FXIa-specific aptamers are used in a method to detect the presence and optionally quantify the amount of FXIa or localize FXIa. For example, the FXIa-specific aptamers can be used to detect the presence of FXIa in a sample. In the context of the present disclosure, a sample is mixture (either already in a liquid or capable of being provided as in a liquid form) suspected of comprising FXIa. The sample can be a solution or a suspension. The sample can be processed into a solution or a suspension. The sample can be a biological sample. Exemplary biological samples include, but are not limited to, bodily fluids (e.g., blood, urine, gastro-intestinal juice, interstitial fluid, lachrymal fluid, sweat, saliva, stools, sputum, pus, cerebrospinal fluid, semen, prostatic fluid, milk, nipple aspirate fluid, lachrymal fluid, perspiration), tissues (swabs (e.g., cheek swabs), tissue biopsy), fractionated bodily fluids (serum, plasma, etc.), cell extracts (e.g., cytoplasmic membrane, mitochondrial extract, nuclear extracts, etc.), cell suspensions, secretions as well as cultures of such biological samples. In order to detect the presence of FXIa in a sample, the aptamers of the present disclosure are admixed with the sample under conditions favoring the formation of a complex between the aptamers and FXIa. In such conditions, the presence of complex between the aptamer and FXIa is indicative of the presence of FXIa in the sample. Still in such conditions, the absence of a complex between the aptamer and FXIa is indicative of the absence of FXIa in the sample. In such method, it is possible to quantify the amount of the FXIa in the sample, especially when the aptamer is modified to be associated with a detectable label (e.g., a radioactive label, an enzymatic label or a fluorescent label for example). By measuring the signal associated with the label, it is possible to determine or estimate the amount complexes formed between the aptamer and FXIa. Alternatively, the label is a solid support and the solid support is washed from the unbound elements of the sample to detect and optionally quantify FXIa.

In another embodiment, the FXIa-specific aptamers can be used in an imaging method to detect the presence and localize FXIa in a subject. In such embodiment, the aptamers of the present disclosure (preferably modified to be associated with a detectable label such as a radioactive label) are administered to the subject under conditions to allow the formation of a complex between the aptamers and FXIa. Since FXIa is mostly located in a clot or in the vicinity of a clot, then, the subject is then submitted to an imaging technique to determine if the detectable label associated with the aptamers localize in one or more areas in the subject. The detection of the label in the individual is indicative of the presence (and optionally the localization) of one or more clots in the subject.

In yet another embodiment, the FXIa-specific aptamers can be used to enrich or purify FXIa from a sample comprising other components than FXIa. In such embodiments, the FXIa-specific aptamers are modified either to bear or be associated with an affinity label. The FXIa-specific aptamers are admixed with the sample (which is preferably a liquid sample) under conditions allowing for the formation of a complex between the FXIa-specific aptamers and FXIa. Then, the complex is retrieved from the sample using the affinity label present on or associated with the aptamers in order to enrich the concentration or even purify FXIa from the sample. Alternatively, the label is a solid support and the solid support is washed from the unbound elements of the sample to enrich or purify FXIa.

Screening Assays Based on Factor XIa-Specific Aptamer

The present disclosure provides FXIa-specific aptamers which can be used as controls to develop additional therapeutics, including additional aptamers, having improved therapeutic or safety properties for the prevention, treatment or the alleviation of symptoms associated with thrombosis in a subject (such as a mammal, e.g., a human).

In an embodiment, the present disclosure provides a method of determining if a putative therapeutic agent (herein referred to as a test agent) would be useful for the prevention, treatment or the alleviation of symptoms of thrombosis in a subject. In order to do so, the test agent is contacted with Factor XIa to obtain a test level of the biological activity of Factor XIa. The contacting step between the test agent and FXIa can be done in vivo (e.g., in a non-human animal) or in vitro. Since FXIa's biological activity is a proteolytic activity, the test level can be obtained by measuring the proteolytic activity of FXIa (in the presence of the test agent) be either determining the amount of an uncleaved substrate of FXIa or a proteolytic product generated by FXIa. In an embodiment, the substrate of FXIa is FIX and the proteolytic product is FIXa. In another embodiment, the substrate is a synthetic substrate of FXIa (e.g., S2366) and the proteolytic product is a chromogenic or fluorescent label of the synthetic substrate. Once the test level has been determined, it is compared to a control level of the biological activity of FXIa. The control level can be derived from or obtained by contacting FXIa with the aptamer described herein, the aptamer variant described herein or the aptamer fragment described herein. In some embodiments, the FELIAP aptamer is used to obtain or derive the control level. Optionally, the method can comprise determining the control level of the biological activity of FXIa and providing the aptamer, the aptamer variant or the aptamer fragment. Once the comparison is made, then it can be determined if the test agent is useful for preventing, treating or alleviating the symptoms associated with thrombosis. If the test level is equal to or lower than the control level (e.g., if the test agent inhibits more the biological activity of FXIa than the aptamers, the aptamer variants or the aptamer fragments), then it is determined that the test agent is useful for preventing, treating or alleviating the symptoms associated with thrombosis. However, if the test level is higher than the control level (e.g., if the test agent inhibits less the biological activity of FXIa than the aptamers, the aptamer variants or the aptamer fragments), then it is determined that the test agent is not useful for preventing, treating or alleviating the symptoms associated with thrombosis.

In another embodiment, the present disclosure provides a method of using the aptamers, the aptamer variants or the aptamer fragments described herein as "leads" to screen for aptamers having improved properties. As such, the present disclosure also provides a method of determining if an aptamer (herein referred to as a test aptamer) would be useful for the prevention, treatment or the alleviation of symptoms of thrombosis in a subject. In some embodiments, the method can be used to screen a library of aptamers having at least one nucleotide substitution, addition or deletion when compared to the aptamers/variants/fragments of the present disclosure. In order to do so, the test aptamer is contacted with Factor XIa to obtain a test level of the biological activity of Factor XIa. The contacting step between the test aptamer and FXIa can be done in vivo (e.g., in a non-human animal) or in vitro. Since FXIa's biological activity is a proteolytic activity, the test level can be obtained by measuring the proteolytic activity of FXIa (in the presence of the test aptamer) be either determining the amount of an uncleaved substrate of FXIa or a proteolytic product generated by FXIa. In an embodiment, the substrate of FXIa is FIX and the proteolytic product is FIXa. In another embodiment, the substrate is a synthetic substrate of FXIa (e.g., S2366) and the proteolytic product is a chromogenic or fluorescent label of the synthetic substrate. Once the test level has been determined it is compared to a control level of the biological activity of FXIa. The control level can be derived from or obtained by contacting FXIa with the aptamer described herein, the aptamer variant described herein or the aptamer fragment described herein. In some embodiments, the FELIAP aptamer is used to obtain or derive the control level. Optionally, the method can comprise determining the control level of the biological activity of FXIa and providing the aptamer, the aptamer variant or the aptamer fragment. Once the comparison is made, then it can be determined if the test aptamer is useful for preventing, treating or alleviating the symptoms associated with thrombosis. If the test level is equal to or lower the control level (e.g., if the test aptamer inhibits more the biological activity of FXIa than the aptamers, the aptamer variants or the aptamer fragments), then it is determined that the test aptamer is useful for preventing, treating or alleviating the symptoms associated with thrombosis. However, if the test level is higher than the control level (e.g., if the test aptamer inhibits less the biological activity of FXIa than the aptamers, the aptamer variants or the aptamer fragments), then it is determined that the test aptamer is not useful for preventing, treating or alleviating the symptoms associated with thrombosis.

The present invention will be more readily understood by referring to the following examples which are given to illustrate the invention rather than to limit its scope.

EXAMPLE

Reagents. The aptamer library comprised a ssDNA template with sequence 5'-GAATTCTAAT ACGACTCACT ATA-$N_{40}$-GCGTCCAACA CATCG-3' (SEQ ID NO: 29). The forward (A) and reverse primers (B) were 5'-GAATTCTAAT ACGACTCACT ATA-3' (SEQ ID NO: 40) and 5'-GCGTCCAACAC ATCG-3' (SEQ ID NO: 41) respectively. These and all other oligonucleotides employed (see Table 2 below for a description of their nucleic acid sequence) were purchased from Integrated DNA Technologies (IDT, Coralville, Iowa). FXI, FXIa, FIX and FXIIa were bought from Enzyme Research Laboratories (South Bend, Ind.). Biotinylated goat anti-human Factor XI (FXI) antibody was purchased from Affinity Biologicals (Ancaster, ON). Dynabeads Biotin Binder was bought from Thermo Fisher Scientific (Waltham, Mass.). For thrombin generation assays (TGA), TGA substrate and TGA calibrator sets were obtained from Technothrombin GmbH (Vienna, Austria). Activated Partial Thromboplastin Time (APTT) reagent was from Diagnostica Stago (Asnieres, France). Chromogenic substrate S2366 was purchased from Instrumentation Laboratory (Lexington, Mass.).

TABLE 2

Nucleotidic sequence of the tested aptamers. The underlined regions of the sequences refer to the "constant primer binding" sites (e.g., the 5' wing or the 3' wing). The italicized regions represent the "variable" domains (e.g., the core region). FXIa inhibitory activity was assessed as the inhibition of amidolytic activity of chromogenic substrate SEQ ID NOs are provided for the entire aptamer as well as the varibale (core) region. S2366. +++ = highest FXIa inhibitory activity, ++ = active FXIa inhibitory activity, + = slightly active FXIa inhibitory activity, - = no FXIa inhibitory activity.

| Designation | Nucleotide sequence | FXIa inhibitory activity | SEQ ID NOs |
|---|---|---|---|
| FELIAP | GAATTCTAATACGACTCACTATAAACCTATCGGACTATTGTTAGTGATTTTTATAGTGTGCGTCCAACACATCG | +++ | 1 and 24 |
| NRMAPT 1 | GAATTCTAATACGACTCACTATATACGTGGTTCTTTTTTTAGGGAGTTCGATCCTGAGGCCTGCGTCCAACACATCG | + | 2 |
| APT10_E | GAATTCTAATACGACTCACTATATGTCACTCTGATCAAAAATTTTGTAGTCATCTTGTTATGCGCGTCCAACACATCG | + | 3 and 69 |
| NRMAPT 3 | GAATTCTAATACGACTCACTATACATAAAAACTATATACGTGGTTCTTTTTTAGTTTTTCGTGCGTCCAACACATCG | - | 4 |
| NRMAPT 4 | GAATTCTAATACGACTCACTATATCTTACATGGCCCCATTATTTTAGAGTTCATTCCGATTGGGCGTCAAACACATCG | - | 5 |
| APT10_D | GAATTCTAATACGACTCACTATAAACCTATCGGACTATTGTTAGTGATTTTTAGAGTGGCGTCCAACACATCG | + | 6 and 30 |
| NRMAPT 6 | GAATTCTAATACGACTCACTATAGCGTATACGTGGTCTTTTTCGCAGGATAGTATGTATTTGCGTCCAACACATCG | - | 7 |
| NRMAPT 7 | GAATTCTAATACGACTCACTATAAACCTATCGTACTATTGTTAGTGATTTTTATAGTGTGCGTCCAACACATCG | - | 8 and 31 |
| APT10_A | GAATTCTAATACGACTCACTATAAACCTATCGGACTATTGTTAGTGATTTTTATAGTTTGCGTCCAACACATCG | ++ | 9 and 32 |
| NRMAPT 9 | GAATTCTAATACGACTCACTATAAACCTATCTGACTATTGTTAGTGATTTTTATAGTGTGCGTCCAACACATCG | - | 10 and 33 |
| NRMAPT10 | GAATTCTAATACGACTCACTATAAACCTATCGGACTATTGTTATTGATTTTTATAGTGTGCGTCCAACACATCG | - | 11 and 34 |
| NRMAPT11 | GAATTCTAATACGACTCACTATACATAAAAACTATATACGTGGTTCTTTTTTAGTTTTTCTTGCGTCCAACACATCG | - | 12 |
| APT10_B | GAATTCTAATACGACTCACTATAAACCTATCGGACTATTGTTAGTGATTTTTATATTGTGCGTCCAACACATCG | ++ | 13 and 35 |
| APT10_C | GAATTCTAATACGACTCACTATAAACCTATCGGACTATTTTAGTGATTTTTATAGTGTGCGTCCAACACATCG | - | 14 and 36 |

TABLE 2-continued

Nucleotidic sequence of the tested aptamers. The underlined regions of the sequences refer to the "constant primer binding" sites (e.g., the 5' wing or the 3' wing). The italicized regions represent the "variable" domains (e.g., the core region). FXIa inhibitory activity was assessed as the inhibition of amidolytic activity of chromogenic substrate SEQ ID NOs are provided for the entire aptamer as well as the varibale (core) region. S2366. +++ = highest FXIa inhibitory activity, ++ = active FXIa inhibitory activity, + = slightly active FXIa inhibitory activity, - = no FXIa inhibitory activity.

| Designation | Nucleotide sequence | FXIa inhibitory activity | SEQ ID NOs |
|---|---|---|---|
| NRMAPT14 | GAATTCTAATACGACTCACTATA*AACCTATTGGACTATTGTTAGTGATTTTTATAGTGT*GCGTCCAACACATCG | − | 15 and 37 |
| NRMAPT15 | GAATTCTAATACGACTCACTATA*CACGTGGTTCTTTATTTAGTTATGTCGTCGTTTTTTCAT*GCGTCCAACACATCG | − | 16 |
| NRMAPT16 | GAATTCTAATACGACTCACTATA*AACCTATCGGACTATTGTTAGTTATTTTTATAGTGT*GCGTCCAACACATCG | − | 17 and 38 |
| NRMAPT17 | GAATTCTAATACGACTCACTATA*AACCTATCGGACTATTGTCAGTGATTTTTATAGTGT*GCGTCCAACACATCG | − | 18 and 39 |
| NRMAPT18 | GAATTCTAATACGACTCACTATA*CATAAAAACTATATACTTGGTTCTTTTTTAGTTTTTCGT*GCGTCCAACACATCG | − | 19 |
| NRMAPT19 | GAATTCTAATACGACTCACTATA*CACAAAAACTATATACCTGGTTCTTTTTTAGTTTTTCGT*GCGTCCAACACATCG | − | 20 |
| NRMAPT20 | GAATTCTAATACGACTCACTATA*AACACACAAACCTATTTTTCGATTTTCCTGCCATCACTCC*GCGTCCAACACATCG | − | 21 |
| NRMAPT21 | GAATTCTAATACGACTCACTATA*CATAAAAACTATATACGTTGTTCTTTTTTAGTTTTTCGT*GCGTCCAACACATCG | − | 22 |

Systemic Evolution of Ligands by Exponential Enrichment (SELEX).

Solution-based SELEX was performed as previously described (Tuerk et al., 1990) with some modifications. In the sequence of the starting ssDNA library, 5'-GAAT-TCTAAT ACGACTCACT ATA-$N_{40}$-GCGTCCAACA CATCG-3' (SEQ ID NO: 29), $N_{40}$ represents a 40 nucleotide randomized region. Before selection, streptavidin-coated magnetic beads (5 μL packed volume) were prewashed five times in Aptamer Folding Buffer (AFB; 20 mM Tris-HCl pH 7.4, 140 mM NaCl, 5 mM KCl, 1 mM $MgCl_2$ and 1 mM $CaCl_2$). All reactions took place at room temperature; washes were performed using a magnet to concentrate the beads at the bottom of the reaction tube. Next, biotinylated goat anti-human factor XI antibody (Affinity Biologicals) was added at quadruple the FXIa concentration to be employed, and incubated for 45 minutes prior to washing. FXIa (60 nM) was then added to the antibody-coated beads and incubated for 1 hour. Five washes were carried out prior to the addition of 1 000 picomoles of aptamer library which had been diluted to 4 nM in AFB and heated to 90° C. for 5 minutes before being cooled on ice. The folded library was then added to the immobilized FXIa and incubated for 1 hour with end-over-end rotation on a Barnstead Thermolyne Labquake. Unbound aptamers were removed by five washes in AFB. Bound aptamers were extracted from protein/antibody/bead assemblies using phenol: chloroform: isoamyl alcohol (71:24:1, vol/vol, saturated with Tris-Cl, Thermo Fisher Scientific) and precipitated with ⅔ vol/vol absolute ethanol to conclude the selection round. The pool of selected aptamers was then PCR-amplified using a high-fidelity heat-stable DNA polymerase (Phusion; Thermo Fisher Scientific) in an asymmetric PCR protocol in which 13-fold more primer A than primer B was employed; the ssDNA sense strand was then purified by preparative agarose gel electrophoresis using a 2% (w/vol) agarose gel and an Ultrafree-DA centrifugal filter unit (Millipore Sigma, Billerica, Mass.) to produce the amplified aptamer library and conclude the first selection round (Round 1). for Round 3, selection stringency was increased by switching from AFB to stringent wash buffer (SWB; 20 mM Tris-HCl pH 7.4, 4 M NaCl, 5 mM KCl, 1 mM $MgCl_2$, 1 mM $CaCl_2$, 0.005% Tween 20) and gradually reducing the incubation time of the library with FXIa such that it was only 15 min in Round 10.

After five rounds of positive selection, the resulting amplified library was combined with beads, biotinylated anti-FXIa, and FXIa as described above, and negatively selected using recombinant His-tagged Kunitz Protease Inhibitor domain of human protease nexin 2 (KPI, 63 amino acids) expressed in *Pichia pastoris* yeast and purified exactly as previously described (Navaneetham et al., 2005), at a concentration of 6.8 μM, to block the FXIa active site. Washing and incubations were as described above for positive selection, except that aptamers from the amplified library not binding to the KPI-FXIa-antibody-bead assemblies were magnetically separated and combined with fresh FXIa, anti-FXI antibodies and magnetic beads to start the next round of selection. Rounds six through ten of SELEX thus combined positively selecting aptamer candidates with unblocked FXIa and negatively selecting against aptamer candidates binding to KPI-blocked FXIa or anti-FXI antibodies or magnetic beads.

High-Throughput Sequencing.

High-throughput (also known as deep) sequencing was employed to characterize the selected aptamer populations following four and ten rounds of SELEX. Single-stranded aptamers generated by asymmetric PCR were PCR-amplified using forward primer 5'-AATGATACGGC GACCAC-CGAG ATCTACACTA GATCGCACAC TCTTTCCCTA CACGACGCTC TTCCGATCTN NNNGAATTCT AATACGACTC ACTATA-3' (SEQ ID NO: 42) and reverse primer 5'-CAAGCAGAAG ACGGCATACG AGAT-TCGCCT TAGTGACTGG AGTTCAGACG TGT-GCTCTTC CGATCTCGAT GTGTTGGACA AGCA-GAAGAC GGCATACGAG ATTCGCCTTA GTGACTGGAG TTCAGACGTG TGCTCTTCCG ATCTCGATGT GTTGGACGCC GC-3' (SEQ ID NO: 43).

The resulting amplicons were sequenced using an Illumina Miseq DNA sequencer at the Farncombe Metagenomics Facility, McMaster University. The raw sequencing data was processed using Illumina's Basespace online NGS platform for tagged sequence pool sorting, and to ensure sequence data output was converted to FASTQ format. Further data processing was as described (Gysbers et al., 2015).

Aptamers.

Figure 6A:
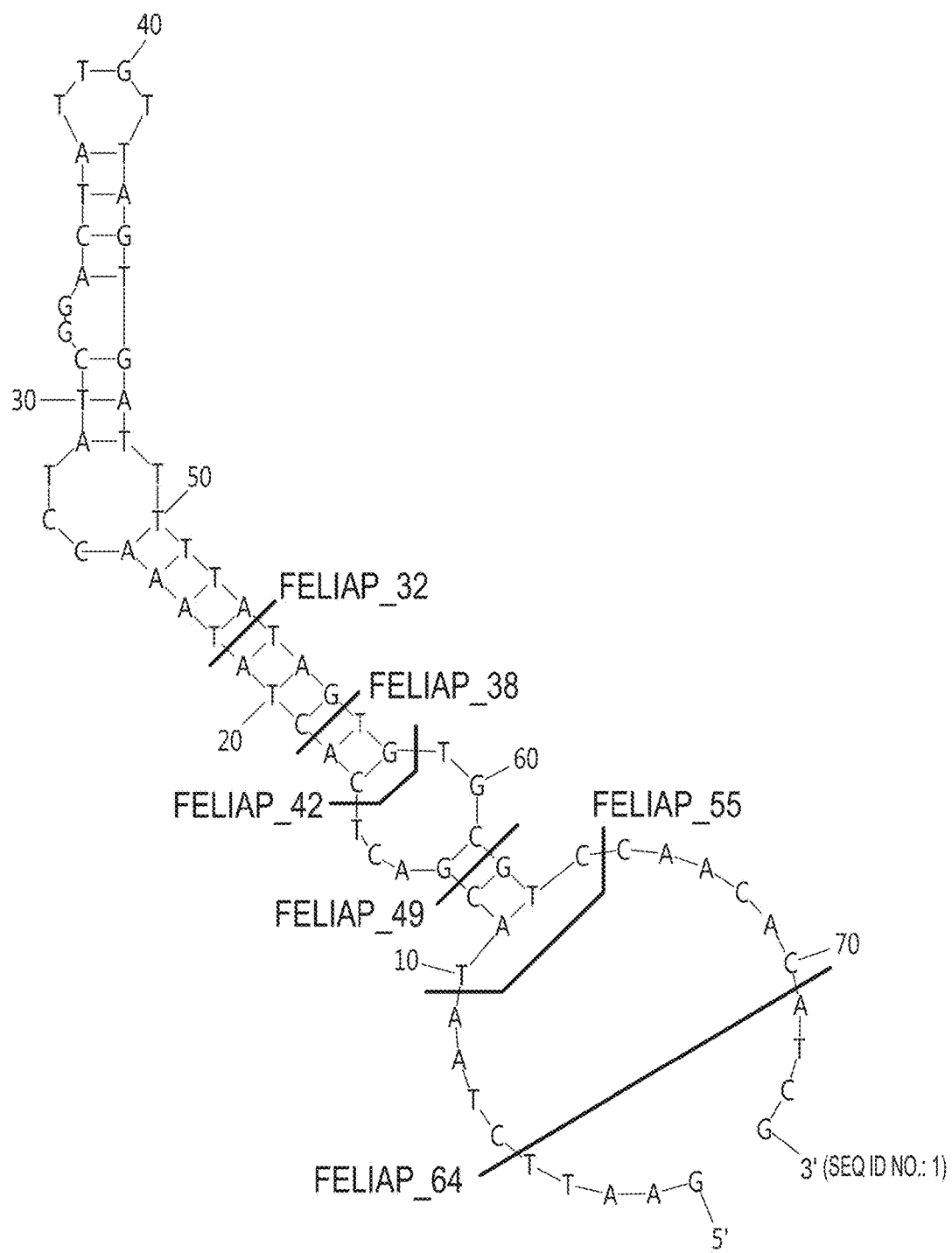
FIGS. 6A and 6B provide the characterization of truncated derivatives of FELIAP as inhibitors of FXIa-mediated amidolysis. (A) Extent of truncation analysis. Sequences to the left of bolded lines crossing the Mfold-generated predicted secondary structure of FELIAP are identified as FELIAP_X, where X=the length of the truncated aptamer (32, 38, 42, 49, 55, 64, or 74 for full-length FELIAP. (B) Means±SEM (n=3) of colour generation following FXIa-mediated amidolysis of chromogenic substrate S2366, in the presence (black bars) of SCRAPT, FELIAP, or truncated derivatives of FELIAP identified in panels A and B, or in the absence of of added DNA molecules (white bar).

The full length FELIAP aptamer sequence was determined to be 5'-GAATTCTAAT ACGACTCACT ATAAAC-CTAT CGGACTATTG TTAGTGATTT TTATAGTGTG CGTCCAACAC ATCG-3' (SEQ ID NO: 1). A control aptamer of the same length but scrambled DNA sequence (SCRAPT) was synthesized for comparative purposes, with sequence 5'-TTCTAATACG ACTCACTATA AGGGAGGGCA GTGGGATGGC GTTAGTGAGG GAGGGTGTGG GGCGTCCAAC ACAT-3' (SEQ ID NO: 44). To generate truncated versions of FELIAP, nucleotides from both the 3' and 5' ends were sequentially removed as depicted schematically in FIG. 6A and presented in Table 4. Before use, all aptamer preparations were diluted into AF buffer, 10 mM Tris-Cl, 1 mM EDTA pH 8.0, Tris-buffered saline, or PPNE kinetics buffer (20 mM sodium phosphate, 100 mM NaCl, 0.1 mM EDTA, 0.1% polyethylene glycol (PEG) 8000, pH 7.4). The diluted aptamers were refolded by heating to 90° C. for 5 min and then cooled for 10 min on ice.

Chromogenic Assay.

Assays were performed in a 96-well flat bottom microtiter plate (Corning Incorporated, Corning, N.Y.) at 37° C. in reaction buffer PPNE. Reactions (200 µL) contained 1 nM FXIa, 90 µM chromogenic substrate S2336 and aptamer concentrations ranging from 0.78 to 10 µM. The rate of substrate hydrolysis was recorded at 405 nm on an ELx808 Absorbance Microplate Reader (Biotek, Winooski, Vt., USA).

FXIa-Mediated FIX Activation.

FIX (6.2 µM) was incubated with 2 nM FXIa in the presence of 10 µM FELIAP, 10 µM scrambled DNA or 2.6 µM KPI in TBS supplemented with 5 mM $CaCl_2$ at 37° C. Samples were incubated for 30 min. Following the 30 min incubation, the reactions were quenched using Sodium Dodecyl Sulphate (SDS) polyacrylamide gel electrophoresis (SDS-PAGE) loading buffer containing dithiothreitol and electrophoresed on a 12% SDS-polyacrylamide gel. Protein bands were visualized by staining with Coomassie Brilliant Blue.

Inhibition of FXIa by Antithrombin.

FXIa (200 nM) was pre-incubated with 10 µM FELIAP or SCRAPT at 37° C. for 5 minutes, and then combined with 2 µM purified human antithrombin in the presence of 2 U/mL sodium heparin (Sigma-Aldrich) for a further 1 or 5 minutes. At the end of the antithrombin incubation time, samples were quenched and subjected to electrophoresis as described above.

FXI Activation Assay.

FXI (700 nM) in PPNE buffer was reacted with 70 nM thrombin in the presence or absence of 1 mg/L dextran sulphate (molecular weight 500 kDa) at 37° C. for 30 minutes in the presence or absence of 10 µM FELIAP or SCRAPT or 1.5 µM recombinant His-tagged hirudin variant 3 (HV3) (Sheffield et al., 2001). At the conclusion of the reaction samples were quenched and subjected to electrophoresis as described above.

Thrombin Generation Assay.

Thrombin generation assays (TGA) were performed using either human normal pooled plasma (NPP) or FXI-depleted plasma (FXI-DP), (Haematologic Technologies, Essex Junction, Vt., USA) with or without supplementation with FXIa. Three variations of TGA were performed, using: human normal pooled plasma (NPP) activated with silicates; FXI-DP activated with tissue factor; and FXI-DP supplemented with FXIa. All TGA reactions were performed in black flat bottom 96-well microtiter plates (Greiner Bio One). In the first protocol, 40 µL of NPP (diluted 1:5 in phosphate-buffered saline (PBS) was mixed with 10 µL of 300 µM FELIAP or SCRAPT) or PBS, 10 µL of APTT reagent (PTT-A, Diagnostica Stago, silica activator diluted 1:20 in PBS), 71 µL of 2 mM TGA substrate solution containing calcium chloride, and 15 µL of PBS, to comprise a total reaction volume of 100 µL. In the second protocol, the APTT reagent was substituted with the prothrombin time reagent Innovin (recombinant human tissue factor (Dade Behring, Deerfield, Ill., USA) and NPP was substituted with FXI-DP. His-tagged recombinant hirudin variant 3 purified from *Pichia pastoris* (Sheffield et al., 2001) served as a positive control for TGA inhibition. In the third protocol, 1 µM FELIAP, SCRAPT, or KPI were combined with 0.71 nM FXIa (10 µL) and pre-incubated for 5 min at room temperature prior to combination with FXI-DP and activation with APTT reagent as in the first protocol. In all protocols, thrombin generation was then followed at 37° C. for 60 min at 1 min intervals using a Fluoroskan Ascent plate reader (Thermo Scientific) set to a wavelength of 380/460 nm. Data was imported into a Microsoft Excel evaluation spreadsheet (www.technoclone.com) for analysis and derivation of TGA test parameters.

Modified APTT assay. APTT assays were performed using a STart 4 coagulometer (Diagnostica Stago) with some modifications. For the reactions, 5 µL of aptamer or PBS buffer control (FELIAP or SCRAPT, 30 µM) was heat-denatured and combined with an equal volume of varying concentrations of purified human FXIa at 37° C. for 3 min. APTT reagent (APTT-XL, 50 uL) was separately preincubated with 45 µL FXI-deficient human plasma under the same conditions, and then clotting was initiated by mixing both sets of components with 50 µL of 71 mM $CaCl_2$ and the clotting time was determined.

Surface Plasmon Resonance (SPR).

Kinetic measurements of aptamer binding were analyzed by SPR on a Biacore T200 (GE Healthcare). To immobilize the aptamer, a CM5 sensor chip (GE Healthcare) was activated with a 0.2 M N-ethyl-N'-(dimethylamino-propyl) carbodiimide (EDC) and 0.05 M N-hydroxysuccinimide (NHS) (Sigma) solution, followed by binding of streptavidin (0.2 mg/ml, pH 4.5). FELIAP and SCRAPT (3' biotinylated) in 100 mM HEPES (pH 7.4), 150 mM NaCl, 0.01% Tween 20 were immobilized on the streptavidin-coated chips at a flow rate of 10 µL/min to 100 response units (RU). Flow cells were regenerated with 0.2% SDS (w/vol). FXIa at concentrations varying from 15.671 nM to 500 nM was injected at a flow rate of 50 µl/min for 180 s to monitor association, and HEPES buffer for 1800 s to monitor dissociation. The signal from the SCRAPT-immobilized flow cell was used as a reference and subtracted from the signal arising from FXIa binding to the FELIAP-immobilized cell. Binding of FXIa and aptamer was quantified by global analysis of on and off rates using the Langmuir 1:1 binding model, as determined with the instrument's software provided by the manufacturer (Biacore). All experiments were done in triplicate.

Selection of FXIa-Binding Aptamer from a Combinatorial Library.

The objective was to select FXIa-inhibiting aptamers from a large library of ssDNA molecules 80 nucleotides in length containing an internal randomized 40 nucleotide region flanked by primer binding sites. Such a library theoretically contains $4^{40}$ different DNA molecules. An in vitro aptamer selection protocol was employed. Initially, only positive selection was employed to enrich for aptamers binding to FXIa. After 4 and 10 rounds of selection, no inhibition of FXIa-mediated amidolysis was noted when the selected aptamer pool was introduced into the reaction (data not shown). Accordingly, the selection protocol was modified by the addition of alternating positive and negative selection steps and rescreened the initial library. The modified protocol included negative selection of aptamers binding to any component of the FXIa-antibody-bead assemblies except the FXIa active site, by introducing the FXIa active site-binding, small protein inhibitor KPI (Navaneetham et al., 2005), after Round 4. In contrast to the initial results, after Round 10, a small but reproducible reduction in amidolysis was observed in the presence of the selected aptamer pool.

Sequencing of the pool after Round 4 indicated that the number of unique sequences had been reduced to 289; Table 3 shows the ten most abundant of these sequences. None elicited any inhibition of FXIa activity when tested individually. The majority of these abundant aptamer sequences contained variable sequences of 21 to 23 nucleotides, rather than the 40 nucleotide variable sequences present in the initial library. By Round 10, the selected pool contained only 79 different sequences, as judged by high-throughput sequencing; eight of the ten most abundant sequences were 36-40 nucleotides long. Two abundant sequences, Apt10-1 and Apt10-3, were also found in the Round 4 pool (Apt4-1 and Apt4-2). When the ten most abundant sequences in the Round 10 pool were tested individually, a single aptamer, Apt10-10, was found to inhibit FXIa-mediated cleavage of chromogenic substrate S2366. This tenth most abundant aptamer sequence in Round 10 was designated Factor ELeven(a) Inhibitory Aptamer (FELIAP). When the initial screen of the aptamer library that involved only positive selection with FXIa was continued in parallel to the positive/negative approach, both anti-FXIa activity of the pool and the presence of FELIAP in the pool were noted at Round 20 (data not shown).

TABLE 3

DNA sequence of the core of the aptamers (name and SEQ ID NOs, column 3) isolated after 4 or 10 rounds of screening (column 1) corresponding to the $N_{40}$ variable domain in the original aptamer library (5'-GAATTCTAAT ACGACTCACT ATA-$N_{40}$-GCGTCCAACA CATCG-3' or SEQ ID NO: 29) is given in column 2. Whether (+) or not (−) the aptamer had inhibitory activity when introduced into FXIa-mediated amidolysis of S2366 is shown in column 4. The ten most abundant sequences obtained after Rounds 4 or 10 are shown in rank order; NT signifies not tested.

| Round | $N_{40}$ Variable sequence | Name, (SEQ ID NO) | FXIa Inhibition |
|---|---|---|---|
| 4 | GCGTCCAACACATCGTATTCAT | Apt4-1 (45) | − |
| 4 | TGGGATGGCGTGGGAGGGCTGTAGGGAGCGTTCAGTGGGT | Apt4-2 (46) | NT |
| 4 | GGGAGGGCGTGGATGGCTGGTGTGAGGTCTTGTGTTTGTT | Apt4-3 (47) | − |
| 4 | GGGAGCGTTCAGTGGGT | Apt4-4 (48) | NT |
| 4 | GCGTCCAACACATCGGATGATAT | Apt4-5 (49) | NT |
| 4 | TGCGTCCAACACATCGTATTCAT | Apt4-6 (50) | NT |
| 4 | TGGGATGGCGTGGGAGGGCTGTAGTGAGCGTTCAGTGGGT | Apt4-7 (51) | NT |
| 4 | CGTCCAACACATCGTATTCAT | Apt4-8 (52) | NT |
| 4 | CTTGCCCACTATCGACTTCACC | Apt4-9 (53) | NT |
| 4 | GCGTCCAACACATCGTAAGTA | Apt4-10 (54) | NT |
| 10 | GCGTCCAACACATCGTATTCAT | Apt10-1 (45) | − |
| 10 | CACTGCGTCCAACACATCGTATTCAT | Apt10-2 (55) | − |
| 10 | TGGGATGGCGTGGGAGGGCTGTAGGGAGCGTTCAGTGGGT | Apt10-3 (46) | − |
| 10 | TGGGATGGCGTGGGAGGGCTGTAGTGAGCGTTCAGTGGGT | Apt10-4 (51) | − |
| 10 | GGGAGGGCGTGGATGGCTGTTGTGAGGTCTTGTGTTTGTT | Apt10-5 (56) | − |

TABLE 3-continued

DNA sequence of the core of the aptamers (name and SEQ ID NOs, column 3) isolated after 4 or 10 rounds of screening (column 1) corresponding to the $N_{40}$ variable domain in the original aptamer library (5'-GAATTCTAAT ACGACTCACT ATA-$N_{40}$-GCGTCCAACA CATCG-3' or SEQ ID NO: 29) is given in column 2. Whether (+) or not (−) the aptamer had inhibitory activity when introduced into FXIa-mediated amidolysis of S2366 is shown in column 4. The ten most abundant sequences obtained after Rounds 4 or 10 are shown in rank order; NT signifies not tested.

| Round | $N_{40}$ Variable sequence | Name, (SEQ ID NO) | FXIa Inhibition |
|---|---|---|---|
| 10 | TGGGATGGCGTGGGAGGGCTGTAGGGAGCGTTT AGTGGGT | Apt10-6 (57) | − |
| 10 | TGGGATGGCGTGGGAGGGCTGTAGTGAGCGTTC ATTGGGT | Apt10-7 (58) | − |
| 10 | GGGAGGGCGTGGATGGCTGGTGTGAGGTCTTGT GTTTGTT | Apt10-8 (47) | − |
| 10 | TGGGATGGCGTGGGAGGGCTGTAGTGAGCGTTT AGTGGGT | Apt10-9 (59) | − |
| 10 | AACCTATCGGACTATTGTTAGTGATTTTTATAGTGT | Apt10-10 (24) | + |

Comparison of FELIAP to Related Aptamer Candidates.

Comparison of FELIAP to the other 78 sequences of lesser abundance found in Round 10 revealed five related aptamers, four of which (Apt10_A through D) were closely related, differing in at most two of 36 positions; the fifth (Apt10_E) was only distantly related by virtue of T-rich areas (38.9% identical—see Table 3). The aligned sequences are shown in Table 1. When these aptamers were tested for their ability to inhibit FXIa amidolysis, FELIAP was found to be the most active and Apt10_E the least active, although all six selected aptamers showed greater inhibitory activity than SCRAPT (FIG. 1A). Modeling of predicted secondary structure using the Mfold web server showed that the portion of FELIAP corresponding to the variable part of the aptamer library likely adopted an extended stem-loop structure containing a bulge separated by two small loops (FIG. 1B). Three of four substitutions correlating with reduced anti-FXIa activity were found in a predicted extended 9 base pair stem structure at the distal end of this structure, while the substitution in APT10_C was at the very apex of the predicted hairpin. As FELIAP was the most potent inhibitor identified in the library, it was employed in all subsequent experiments.

Kinetic Characterization of FELIAP as an Inhibitor of FXIa-Mediated Amidolysis and Clotting.

Figure 2B:
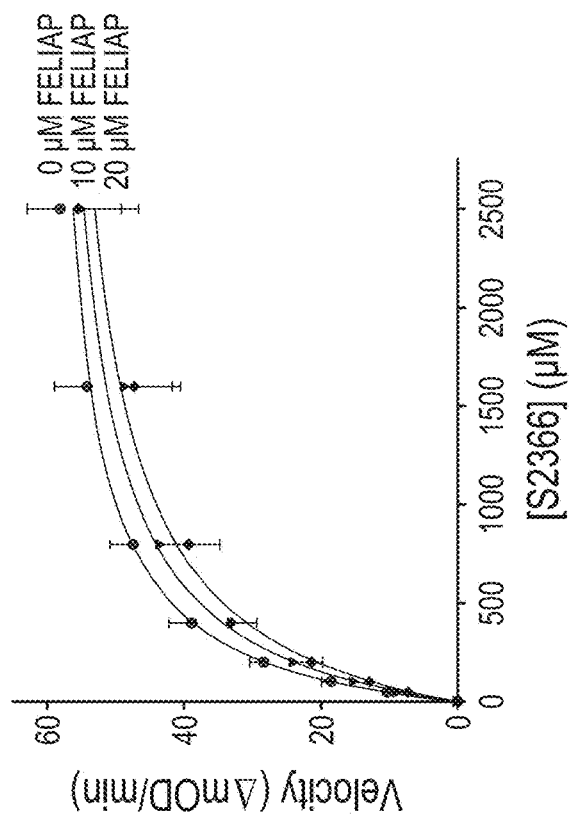
FIGS. 2A to 2D provide the kinetic characterization of FELIAP inhibition of FXIa-mediated amidolysis. (A) Means±SEM (n=3) of reaction velocity for FXIa-mediated amidolysis of S2366 versus aptamer concentration (FELIAP, circles; SCRAPT, squares). (B) Means±SEM (n=3) of reaction velocity versus S2366 concentration in the presence of 0, 10, or 20 µM FELIAP. (C) Lineweaver-Burke transformation of data in (B). (D) Means±SEM (n=7) of modified APTT assays in which FELIAP or SCRAPT were pre-incubated with FXIa, at concentrations given on the x axis, prior to dilution into recalcified FXI-deficient plasma.
Figure 2A:
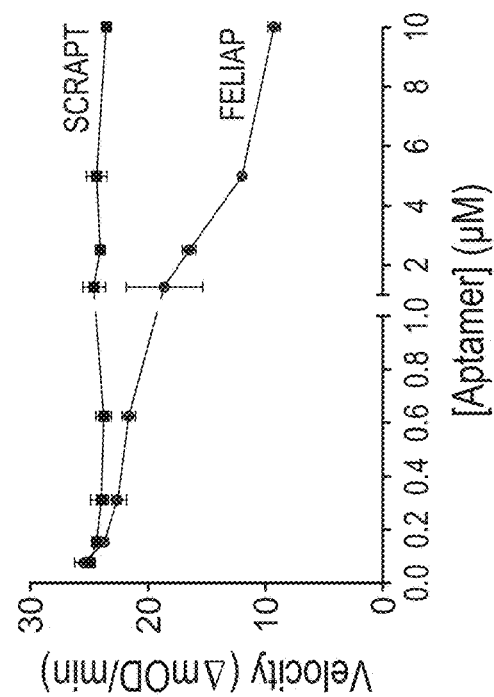
Figure 2D:
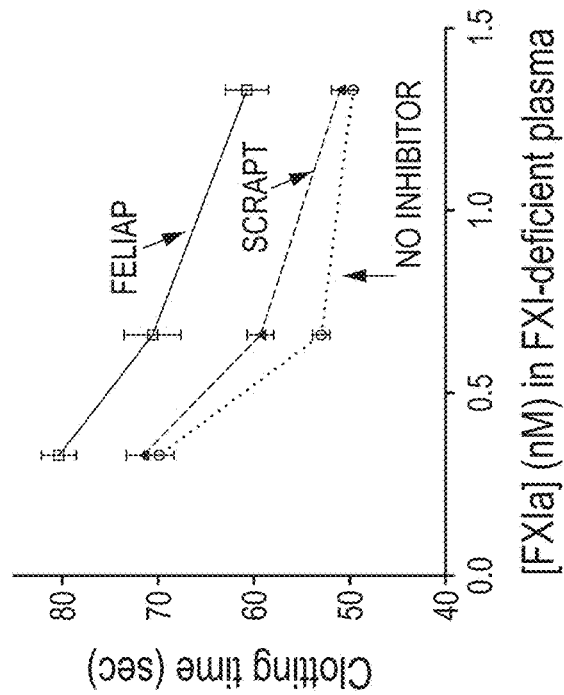
Figure 2C:
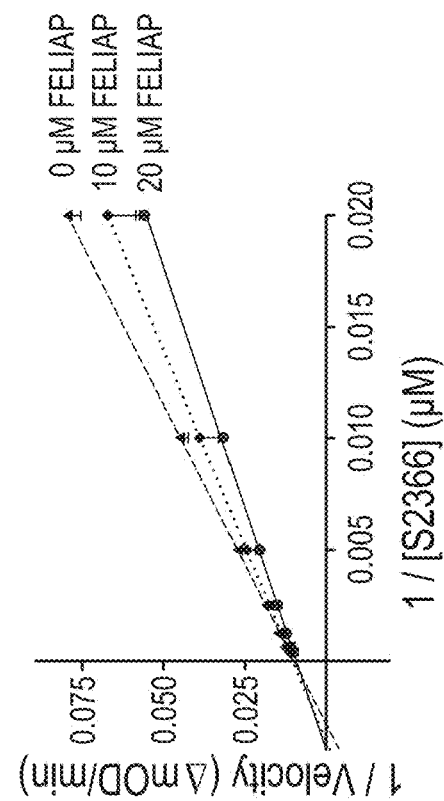

The mode of inhibition of FELIAP was investigated by fixing the concentrations of chromogenic substrate and FXIa and increasing the concentration of FELIAP and measuring the rate of substrate cleavage. A dose-dependent reduction in the reaction rate was observed as FELIAP was increased from 0 to 20 µM, while the same concentrations of SCRAPT had no inhibitory effect (FIG. 2A). Next, the concentration of chromogenic substrate S2366 was varied while keeping FXIa constant at different concentrations of FELIAP (FIG. 2B). The reaction demonstrated competitive inhibition, as suggested by the apparent lack of alteration of the maximum reaction velocity (FIG. 2B) with increasing FELIAP concentrations, and by the common y intercept on the Lineweaver-Burke transformation of the velocity versus substrate curves for increasing FELIAP concentrations (FIG. 2C). Fitting the curves to a competitive inhibition model yielded an estimated Ki for FELIAP of 29 µM by non-linear regression.

Prior to examining the inhibitory effects of FELIAP on FXIa-mediated interactions with specific macromolecular substrates, the capacity of FELIAP to inhibit FXIa-induced clotting in plasma was examined. FXIa was pre-incubated with buffer, FELIAP, or SCRAPT, and combined with FXI-deficient plasma and APTT reagent containing kaolin and cephalin, and recalcified. As shown in FIG. 2D, at all three FXIa concentrations tested, FELIAP delayed plasma clot formation to a greater extent than SCRAPT or buffer controls.

Effects of FELIAP on Macromolecular Reactions of FXI and FXIa.

Figure 3C:
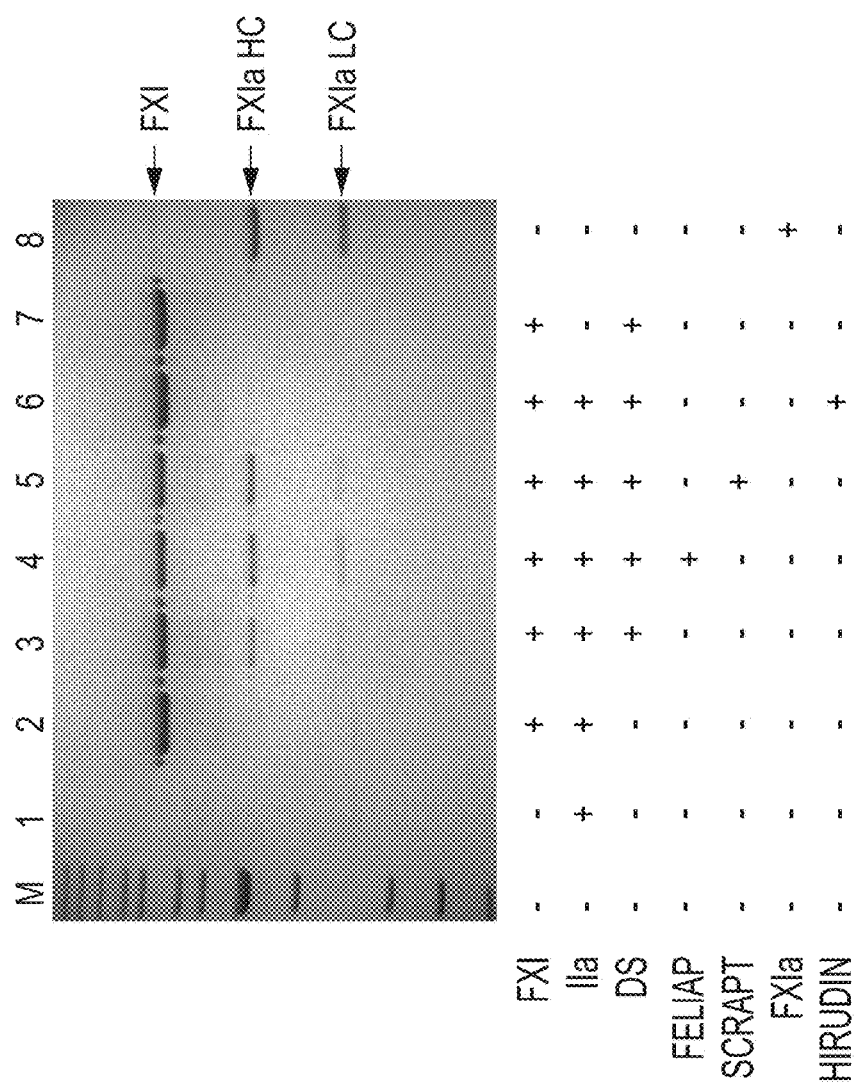

FXIa activates FIX by cleaving two peptide bonds, one at Arg145-Ala146, and the other at Arg180-Val181 of the FIX polypeptide30. This reaction liberates a glycosylated activation peptide (Ala146-Arg180, 10 kDa), and a disulphide-linked γ-carboxylated light chain (Tyr1-Arg145, 71 kDa) and heavy chain (Val181-Thr405, 30 kDa)31,32. An intermediate product comprised of the activation peptide linked to the heavy chain (Ala146-Thr405, 40 kDa) may also be detected. FIG. 3A shows that FXIa-mediated FIX activation was unaffected by SCRAPT (compare heavy and light chains, lanes 1 and 2), while introduction of excess FELIAP (lane 3) or KPI (lane 4) reduced FIXa generation to background levels (lane 5, no FXIa added).

FXIa also reacts with its natural inhibitor, antithrombin, in a reaction that is accelerated by heparin, to form a denaturation-resistant complex between the FXIa active site and the reactive centre of antithrombin, in which the light chain of FXIa (Ile370-Val607) is joined to antithrombin residues His1-Arg393 via an acyl linkage10,33. FIG. 3B shows SDS-PAGE evidence of this 90 kDa complex after 1 or 5 minutes of reaction (lanes 2 and 3) and in the presence of excess SCRAPT (lanes 6 and 7) but not in the presence of excess FELIAP (lanes 4 and 5).

Having demonstrated that FELIAP inhibited the action of FXIa on two macromolecular substrates, FIX and antithrombin, it was then determined if it had any effect on the activation of FXI by thrombin. In the presence of cofactor dextran sulphate (FIG. 3C, lane 3), but not its absence (lane 2), FXI was efficiently activated into FXIa, as previously reported. No inhibition of this reaction was noted in the presence of either excess FELIAP (lane 4) or SCRAPT (lane 5), but activation of FXI was abrogated in the presence of excess hirudin, a potent thrombin inhibitor (lane 6). FELIAP therefore inhibited FXIa-dependent but not FXI-dependent reactions.

Inhibition of Thrombin Generation in Plasma by FELIAP.

Figure 4A:
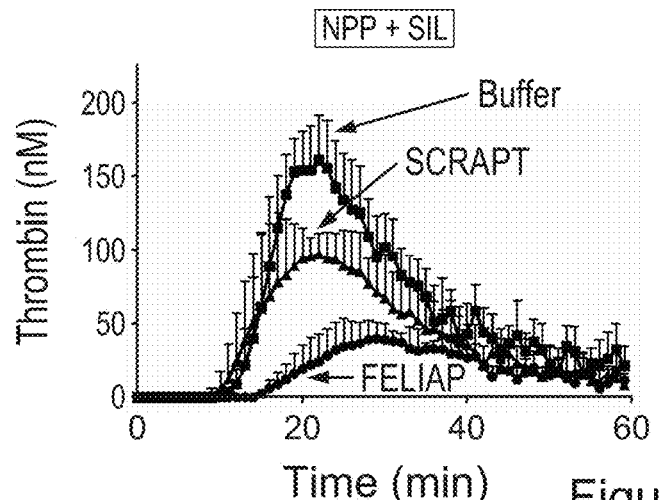
FIGS. 4A to 4I show the inhibition of thrombin generation by FELIAP. Thrombin generation assays (TGA) were conducted in 3 different ways: in recalcified human normal pooled plasma (NPP) using micronized silica (SIL) for contact activation as the initiator (NPP+SIL, panels A-C); in FXI-depleted plasma (FXI-DP) using tissue factor for extrinsic pathway activation as the initiator (FXI-DP+TF, panels D-F); and following 0.25 nM FXIa preincubation with Buffer, 1 µM SCRAPT, or 1 µM FELIAP, in FXI-DP activated with micronized silica (FXI-DP+FXIa+SIL). Thrombin concentration was determined fluorescently every minute for 60 minutes in each case. (A) TGA progress curves (mean±SD (n=6) with addition of agents (Buffer, 30 µM FELIAP, or 30 µM SCRAPT) as indicated by labels and arrows. Upwards error bars are shown. (B) As in (A), but n=5, and with the addition of 2 µM recombinant hirudin variant 3 (hirudin). (C) As in (B), with the addition of agents (Buffer, 2 µM FELIAP, or 2 µM SCRAPT, or 2 µM KPI. Each set of thrombograms are quantified with respect to endogenous thrombin potential (the area under the thrombogram curve) (B, E, H) and time to peak thrombin (C, F, I) below the progress curve panels. Bar graphs are derived from analysis of individual thrombogram curves corresponding to plasma supplementation with Buffer (white), SCRAPT (grey), FELIAP (black), or, in some reactions KPI or Hirudin (light grey). Symbols (above the error bars) indicate statistically significant differences from Buffer reactions, while symbols above the horizontal bar indicate statistically significant differences between SCRAPT- and FELIAP-supplemented and other reactions: p<0.001, ; p<0.001, *.
Figure 4B:
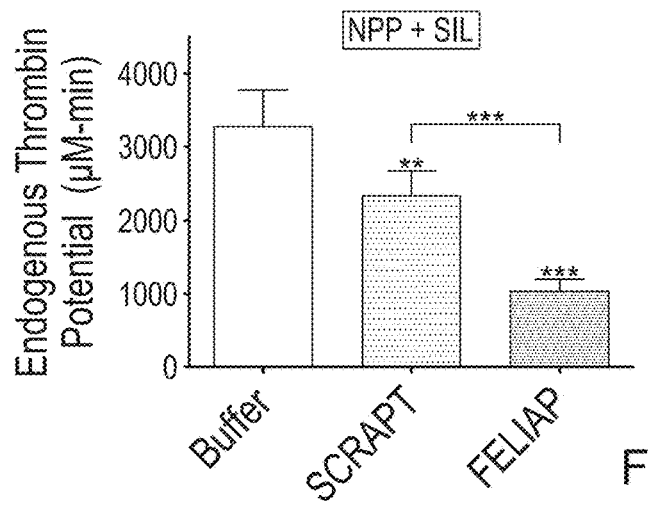
Figure 4C:
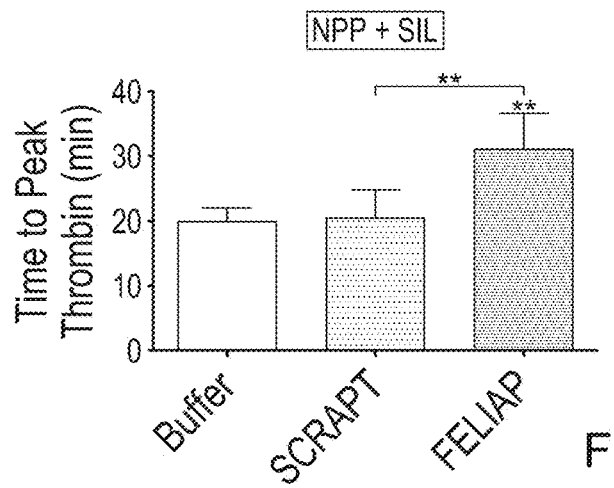

Recalcified dilute normal human pooled plasma, in which the contact pathway of coagulation was activated by micronized silica, was employed to assess the effects of FELIAP on thrombin generation. The thrombin generation assay (TGA) provides information on the timing and kinetics of thrombin generation in plasma using a thrombin-specific fluorogenic substrate and calibrators unaffected by fibrin clot formation, using standardized analytic methods and parameters35. As shown in FIG. 4A, FELIAP had greater effects on thrombin generation in recalcified dilute plasma than SCRAPT. Firstly, 30 µM FELIAP prolonged the lag time of thrombin generation relative to either 30 µM SCRAPT or buffer controls (data not shown). Similarly, FELIAP reduced the endogenous thrombin potential (ETP; the area under the thrombin generation curve) by 3.2-fold, versus 1.4-fold for SCRAPT (FIG. 4B; both reductions p<0.001). Finally, the mean time to peak thrombin was increased 1.5-fold by FELIAP but was unaffected by SCRAPT (FIG. 4C).

Figure 4D:
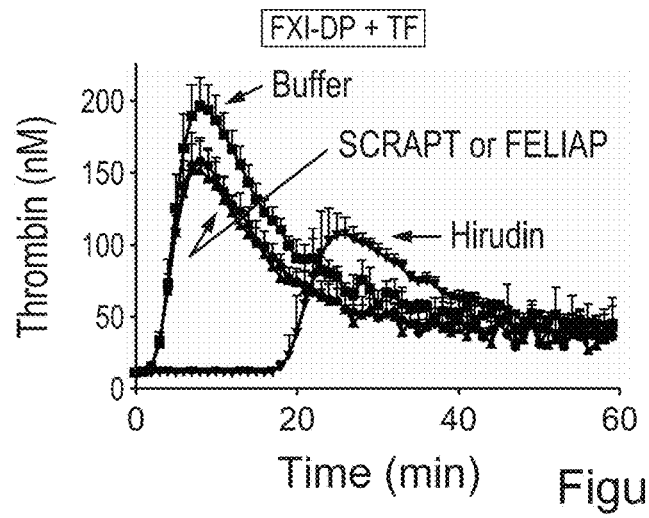
Figure 4E:
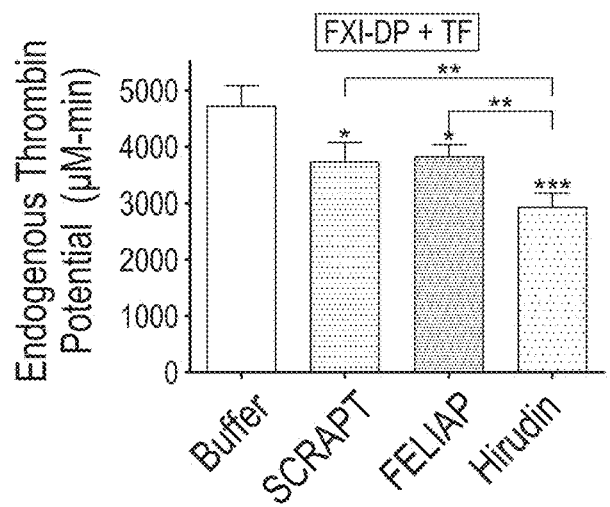
Figure 4F:
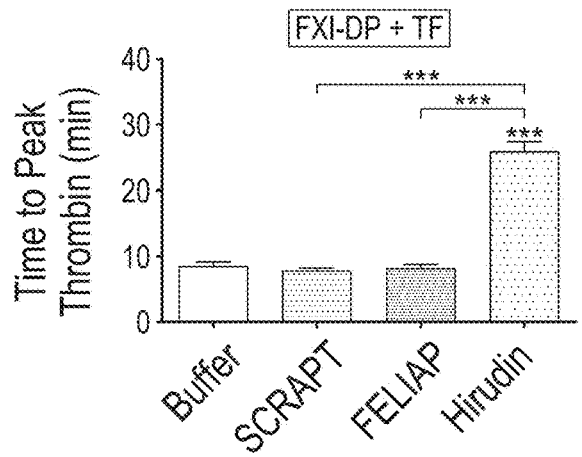
Figure 4G:
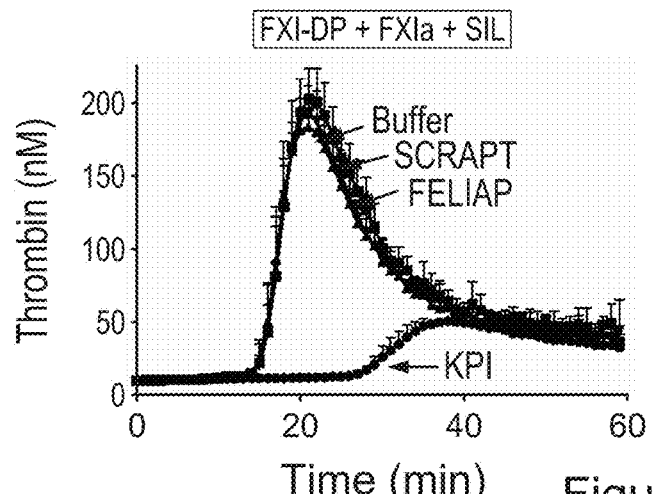
Figure 4H:
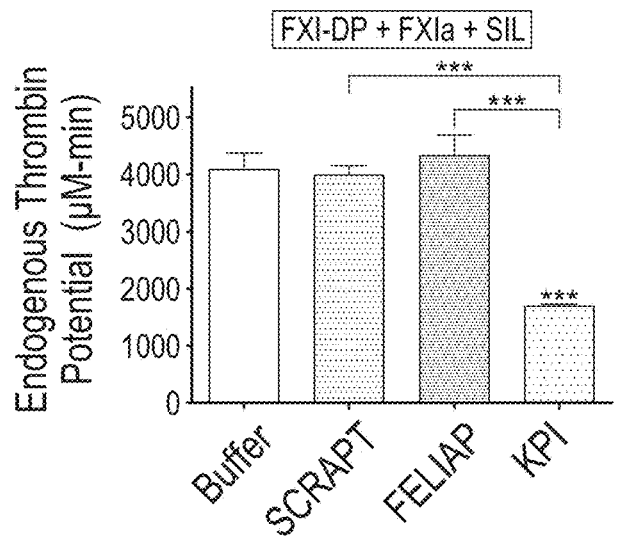
Figure 4I:
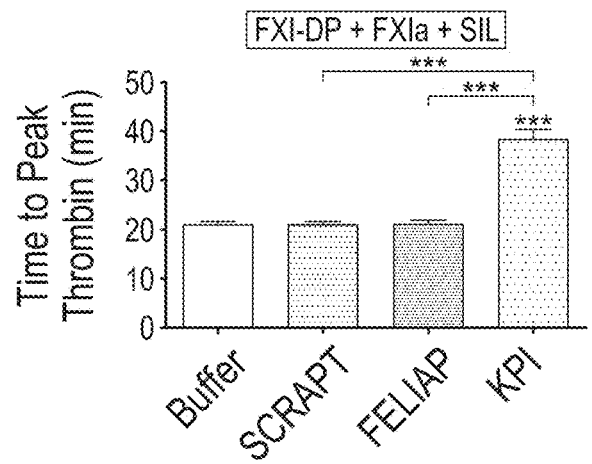

The partial anticoagulant activity observed for SCRAPT in silica-activated TGA using normal pooled plasma was also noted for other single-stranded oligonucleotides of similar length (70-80 nucleotides; data not shown) at equimolar concentrations. To ascertain whether or not this phenomenon was related to FXIa inhibition, TGA was repeated, substituting FXI-depleted plasma for normal plasma and tissue factor for silicates as activators (FIG. 4D). SCRAPT or FELIAP exhibited indistinguishable 1.24- to 1.27-fold reductions in endogenous thrombin potential relative to buffer under these conditions (FIG. 4E), but unaltered times to peak thrombin (FIG. 4F). In contrast, the specific thrombin inhibitor hirudin, at 200 nM, elicited a significantly greater reduction in ETP than 30 µM FELIAP or SCRAPT, and extended the time to peak thrombin by 3.1-fold (p<0.001 versus FELIAP, SCRAPT or buffer, FIG. 4F). SCRAPT or FELIAP effects were eliminated when the aptamers (1.0 µM) were combined with 0.71 nM FXIa and then combined with FXI-depleted plasma activated by silicates (FIGS. 4G-1). In contrast, substitution of KPI for either aptamer significantly reduced the ETP and the time to peak thrombin (FIGS. 4G-1). FELIAP therefore inhibited TGA to a greater extent than SCRAPT in plasma activated via the contact pathway, but not the extrinsic pathway, but to a considerably lesser extent than KPI.

Use of Surface Plasmon Resonance (SPR) to Characterize FEL/AP Binding to FXIa.

Figure 5:
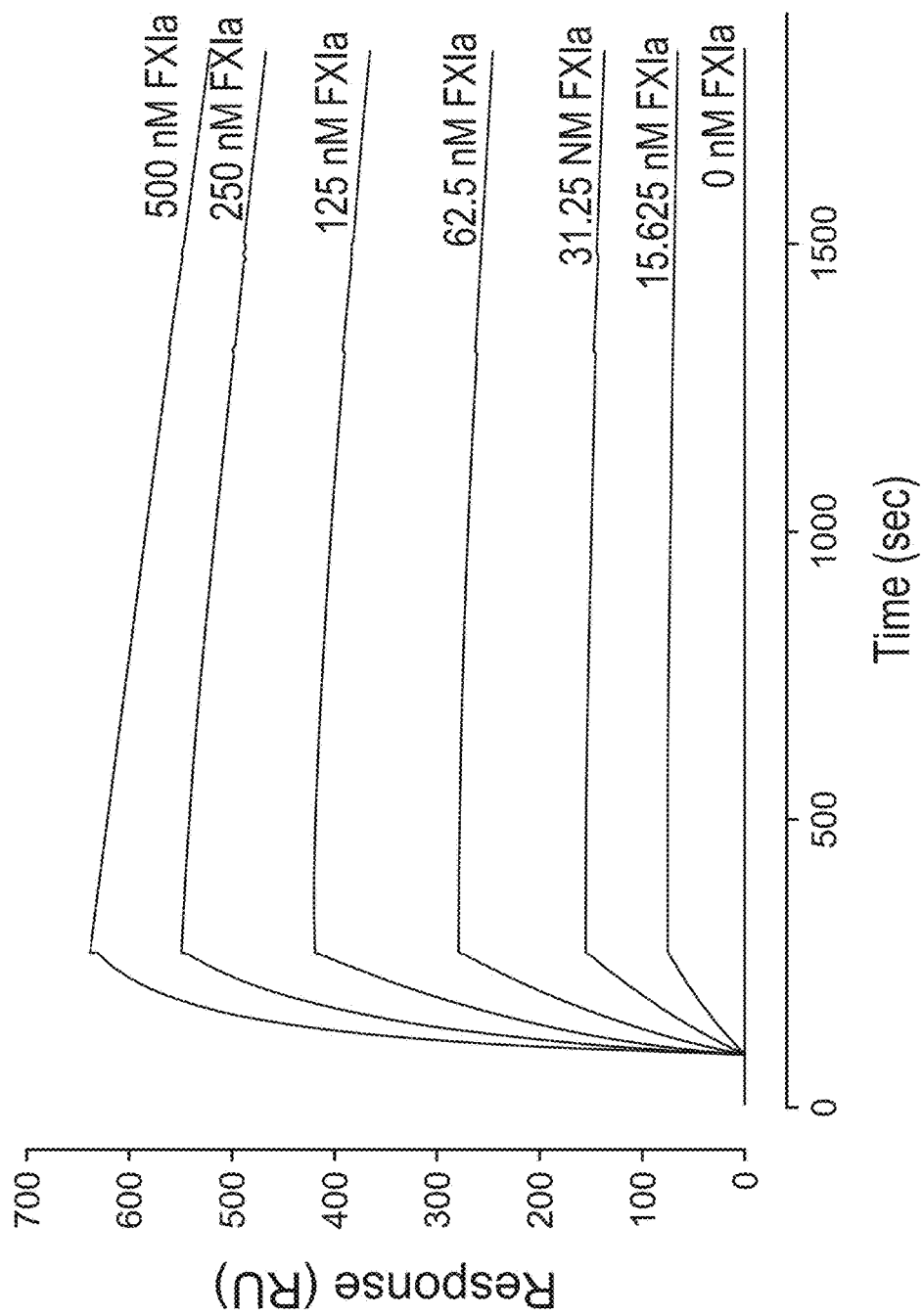
FIG. 5 illustrates the binding of FELIAP to immobilized FXIa. An SPR sensogram showing the interactions between 3'biotinylated FELIAP immobilized on a streptavidin-coated chip and FXIa at 25° C. at FXIa concentrations given above each progress curves. Association was allowed to proceed for 180 seconds followed by 1800 seconds of dissociation. All curves were corrected for non-specific effects by signal subtraction using a reference cell containing 3' biotinylated SCRAPT immobilized on a streptavidin-coated chip. A single dilution series of curves representative of a total of 3 others is shown.

FELIAP and SCRAPT were biotinylated at their 3' ends and immobilized on a streptavidin-coated gold chip. Immobilized SCRAPT served as the reference cell. When increasing concentrations of FXIa from 0 to 500 nM were flowed over these surfaces, increasing response unit binding isotherms were generated when the difference between immobilized FELIAP and immobilized SCRAPT binding was plotted (FIG. 5). It should be noted that the maximum response for SCRAPT binding did not exceed 71 response units at 500 nM FXIa, 1800 seconds (data not shown). The net binding isotherm was characterized by relatively rapid association kinetics and very slow dissociation kinetics. Analysis of these isotherms yielded values for dissociation rate constant (Kd) and the association rate constant (Ka), permitting calculation of the equilibrium binding constant KD, which is Kd divided by Ka. Ka values of $5.2\pm0.1\times10^4$ $M^{-1} S^{-1}$, Kd values of $9.5\pm0.1\times10^{-5}$ $S^{-1}$, and KD values of $1.8\pm0.1\times10^{-9}$ M were obtained (mean±SD of three determinations).

Effects of Progressive Truncation of FELIAP on Inhibition of FXIa-Mediated Amidolysis.

Figure 6B:
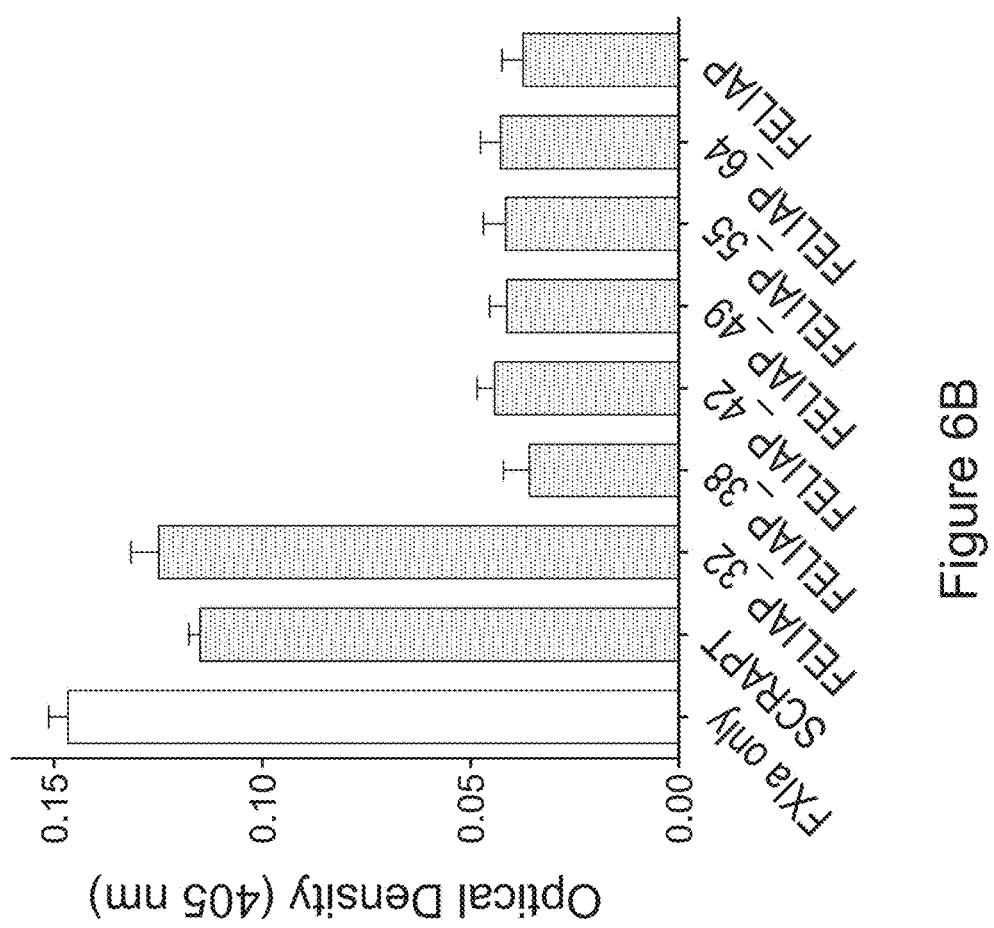

To determine the minimum active sequence of FELIAP required for inhibition of FXIa, several truncated forms of FELIAP were synthesized, using the predicted structure of the aptamer to delete predicted loops and stems progressively. The truncated sequences ranged from 32 to 64 nucleotides long (compared to 74 for full-length FELIAP), were designated FELIAP_X (where X=32, 38, 49, 56 and 64), and constituted 5' and 3' deletion mutants of FELIAP (see Table 4 as well as FIG. 6A). As shown in FIG. 6B, deletion of two predicted loop structures and an intervening short stem (in FELIAP_38) had no effect on anti-FXIa activity. However, reduction of the predicted terminal stem structure from seven (in FELIAP_38) to four base pairs (in FELIAP_32) reduced anti-FXIa activity to background levels equivalent to SCRAPT.

TABLE 4

DNA sequence of truncated aptamers used to provide the results of FIG. 6. The underlined regions of the sequences refer to the "constant primer binding" sites (e.g., the 5' wing or the 3' wing) while the italicized regions refer to the core region.

| Name (SEQ ID NO) | Nucleotide sequence | SEQ ID NO |
|---|---|---|
| FELIAP | GAATTCTAATACGACTCACTATAAACCTATCGGACTA *TTGTTAGTGATTTTTATAGTGT*GCGTCCAACACATCG | 1 |
| FELIAP_64 | CTAATACGACTCACTATAAACCTATGGA *CTATTGTTAGTGATTTTTATAGTGT*GCGTCCAACAC | 60 |
| FELIAP_55 | TACGACTCACTATAAACCTATCGGACTA *TTGTTAGTGATTTTTATAGTGT*GCGTC | 61 |
| FELIAP_49 | GACTCACTATAAACCTATCGGACTATTG *TTAGTGATTTTTATAGTGT*GC | 62 |
| FELIAP_42 | CACTATAAACCTATCGGACTATTGTTAG *TGATTTTTATAGTG* | 63 |
| FELIAP_38 | CTATAAACCTATCGGACTATTGTTAGTG *ATTTTTATAG* | 64 |
| FELIAP_32 | TAAACCTATCGGACTATTGTTAGTGATT *TTTA* | 65 |

Aptamers from combinatorial libraries can be selected to bind virtually any protein of interest. Here, the selection and characterization of FELIAP, a FXIa-binding DNA aptamer was described. The protocol used favoured the selection of aptamers binding at or near the active site of FXIa over those binding to other portions of the enzyme. Several lines of indirect evidence support the conclusion that this strategy was successful. Firstly, FELIAP acted as a competitive inhibitor of chromogenic substrate S2366, which is a tripeptide nitroanilide compound (pyroglutamyl-prolyl-arginyl-p-nitroanilide) which must, by virtue of its small size, enter the interior of the FXIa active site pocket to be cleaved and liberate the coloured product nitroanilide. Secondly, it inhibited two different FXIa-dependent reactions: FXIa-mediated activation of FIX; and FXIa-mediated formation of FXIa-antithrombin complexes. While this observation does not per se exclude an allosteric effect of FELIAP on FXIa, it renders it less likely than active site binding. Thirdly, FELIAP had no effect on FXI activation, further indicating specificity for FXIa, one of whose cardinal features is the active site. Taken together, these data suggest that FELIAP binds specifically to FXIa at or near its active site, with high affinity consistent with the observed nanomolar KD.

KPI was employed to obscure the active site of FXIa in KPI-FXIa-anti-FXI-bead assemblies for negative selection, reasoning that depletion of the aptamer library of candidates binding to any of the constituent parts of these assemblies would enrich for those binding the FXIa active site. KPI is the Kunitz protease inhibitor domain of protease nexin 2, which is an isoform of the β-amyloid precursor protein (APP) secreted from α-granules on platelet activation. The 57 amino acid KPI domain accounts for all of the FXIa-inhibitory activity of APP36 and has been crystallized in complex with FXIa28. The crystal structure revealed that two loops in KPI formed extensive contacts with FXIa; in particular residues in the KPI Thr11-Arg20 loop extend into the substrate pocket, rationalizing the high affinity binding evidenced by reported Ki values of 300-500 µM. While it may seem somewhat circular to use a polypeptide active site inhibitor to identify a ssDNA aptamer inhibitor, aptamers provide multiple potential advantages over proteinaceous inhibitors with respect to immunogenicity, cost of production, antidote generation, and the potential to fine-tune binding via mutagenesis.

While to our knowledge no aptamers to FXI or FXIa have been previously described in the biomedical literature, several aptamers to other coagulation factor targets have been isolated.

Among RNA aptamers, RNA 16.3 bound FVII or FVIIa with KD values of 10-13 nM, inhibiting the enzyme by disrupting tissue factor-FVII(a) complex assembly. A truncated form of a selected RNA aptamer designated 9.3t was found to bind FIXa with a KD of 0.58 nM38, specifically at an extended substrate binding position, or exosite. RNA11F7t aptamer bound FXa with a reported KD of 1.1 nM and inhibited prothrombinase activity by interfering with the interaction between FXa and FVa, while R4CxII-1t bound FXII or FXIIa with KD values of 8.9 and 0.4 nM, respectively, by interfering with FXII and anionic binding. RNAR9D-14T bound thrombin or prothrombin with KD values of 1 or 10 nM via anion binding exosite I. With respect to DNA aptamers, the only ones described to date that target coagulation factors are HD1 and HD22, which bind prothrombin with KD values of 7.1 and 2.4 nM, via exosites I and II, respectively. All previously described aptamers targeting coagulation factors, therefore, act at sites distinct from the active site of these serine proteases. The fact that FELIAP, which acts at or near the active site of FXIa, may have been facilitated by the use of KPI in negative selection, as screening protocols employed in previously published studies used only positive selection. Although the time- and labour-intensive nature of aptamer library screening precluded a systematic analysis, anecdotally FELIAP selection was observed within ten rounds of screening with positive and negative steps, but not until twenty rounds of screening with positive steps alone.

Although SELEX and SELEX-related aptamer screening protocols have been employed to isolate aptamers that bind to their targets with high affinity, numerous limitations need to be overcome for successful application of this biotechnological approach. These include interference from non-degenerate sequences flanking the variable regions in the aptamer library; non-specific retention of sequences not binding the desired target; and accumulation of amplification artifacts and artifactual sequences arising from library regeneration. Many examples of such artifacts were observed using high throughput sequencing after Round 4, some of which persisted to Round 10, as well as the selection of aptamers with barely detectable affinity for FXIa (e.g. Apt10_E). Our results are therefore consistent with the known limitations of SELEX.

Inspection of the Mfold generated secondary structural folding prediction showed that the extended stem-loop structure predicted for FELIAP encompassed more than the variable region nucleotides 24 to 59. FELIAP_38 retained all of full-length FELIAP's anti-FXIa activity, but only three additional base pairs in a predicted terminal stem than non-inhibitory FELIAP_32. These results, taken together with the finding that mutation of the guanosine residue at the predicted turn of the hairpin at nucleotide 40, support the secondary structure model and likely indicate that the AT-rich stem disrupted in FELIAP_32 must be stabilized by additional A-T hydrogen bonds or by the C-G bonding between residues 19 and 56 in FELIAP_38. It is likely that this stem stabilizes the "loop-bulge-loop" conformation of FELIAP_38 for direct contact with FXIa. Localization of the aptamer within the FXIa active site by cross-linking, modeling or co-crystallization will in future be used to test this working hypothesis and to provide clues to how to increase its potency as an inhibitor to match its high affinity as a FXIa ligand.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Buller H R, Bethune C, Bhanot S, Gailani D, Monia B P, Raskob G E, Segers A, Verhamme P, Weitz J I; FXI-ASO TKA Investigators. Factor XI antisense oligonucleotide for prevention of venous thrombosis. N Engl J Med. 2015 Jan. 15; 372(3):232-40.

Gysbers, R., Tram, K., Gu, J. & Li, Y. Evolution of an Enzyme from a Noncatalytic Nucleic Acid Sequence. Sci Rep 5, 11405 (2015).

Navaneetham, D. et al. Structural and mutational analyses of the molecular interactions between the catalytic domain of factor XIa and the Kunitz protease inhibitor domain of protease nexin 2. J Biol Chem 280, 36165-36175 (2005).

Sheffield, W. P., Smith, I. J., Syed, S. & Bhakta, V. Prolonged in vivo anticoagulant activity of a hirudin-albumin fusion protein secreted from *Pichia pastoris*. Blood Coagul Fibrinolysis 12, 433-443 (2001).

Tripodi A. Thrombin generation assay and Its application in the clinical laboratory. Clin Chem. 2016 May; 62(5):699-707.

Tuerk, C. & Gold, L. Systematic evolution of ligands by exponential enrichment: RNA ligands to bacteriophage T4 DNA polymerase. Science 249, 505-510 (1990).

What is claimed is:

1. An aptamer having the structure of formula (I):

$$5'-5W-C-3W-3' \quad (I)$$

wherein:

"-" refers to a nucleotide bond;

5W has the following first nucleic acid sequence:

(SEQ ID NO: 66)
$N_{17}N_{18}N_{19}N_{20}N_{21}N_{22}N_{23}N_{24}N_{71}N_{26}N_{27}N_{28}AN_{29}N_{30}TA$;

C has nucleic acid sequence of SEQ ID NO: 24, 30, 32, 35, 36 or 69;

3W can be present or absent and when present has the following third nucleic acid sequence:

(SEQ ID NO: 67)
$5'-N_{31}N_{32}N_{33}N_{34}N_{35}N_{36}N_{37}N_{38}N_{39}N_{40}N_{41}-3'$;

and the nucleotides at position 14 to 18 ($N_{29}TN_{30}TA$) of SEQ ID NO: 66 are capable of base pairing with the nucleotides at position 33 to 29 of SEQ ID NO: 24, 30, 32, 35, 36 or 69.

2. The aptamer of claim 1 having the nucleic acid sequence of SEQ ID NO: 64.

3. The aptamer of claim 1, wherein, the nucleotides at positions 12 and 13 of SEQ ID NO: 66 are capable of base pairing with the nucleotides at position 35 to 34 of SEQ ID NO: 24, 30, 32, 35, 36 or 69.

4. The aptamer of claim 3 having the nucleic acid sequence of SEQ ID NO: 63.

5. The aptamer of claim 1, wherein the nucleotides at position 8 to 11 of SEQ ID NO: 66, or at position 1 to 5 of SEQ ID NO: 67 are capable of base pairing with the nucleotide at position 2 ($N_{32}$) of SEQ ID NO: 67.

6. The aptamer of claim 5 having the nucleic acid sequence of SEQ ID NO: 62.

7. The aptamer of claim 3, wherein the nucleotides at position 5 to 7 of SEQ ID NO: 66 and at position 3 to 5 of SEQ ID NO: 67 are present, and the nucleotides at position 6 to 7 ($N_{22}N_{23}$) of SEQ ID NO: 66 are capable of base pairing with the nucleotides at positions 4 to 3 ($N_{34}N_{33}$) of SEQ ID NO: 67.

8. The aptamer of claim 7 having the nucleic acid sequence of SEQ ID NO: 61.

9. The aptamer of claim 1 having the nucleic acid sequence of SEQ ID NO: 60.

10. The aptamer of claim 1, wherein 5W has the following first nucleic acid sequence:

(SEQ ID NO: 25)
5'-$N_{12}N_{13}N_{14}N_{15}N_{16}N_{17}N_{18}N_{19}N_{20}N_{21}N_{22}N_{23}N_{24}N_{71}N_{26}$ $N_{27}N_{28}AN_{29}TN_{30}TA$ 3';

C has the nucleotide sequence of SEQ ID NO: 24, 30, 32, 35, 36 or 69;

3W is present and has the following third nucleotide sequence:

(SEQ ID NO: 27)
5'-$N_{31}N_{32}N_{33}N_{34}N_{35}N_{36}N_{37}N_{38}N_{39}N_{40}N_{41}N_{42}N_{43}N_{44}N_{45}$-3';

"-" refers to a nucleotide bond;

the nucleotides at position 17 to 23 ($N_{28}AN_{29}TN_{30}T$) of SEQ ID NO: 25 are capable of base pairing with the nucleotides at positions 35 to 27 of SEQ ID NO: 24, 30, 32, 35, 36 or 69; and the nucleotides at position 6 to 8 ($N_{22}N_{23}N_{24}$) of SEQ ID NO: 25 are capable of base pairing with the nucleotides at position 4 to 2 ($N_{34}N_{33}N_{32}$) of SEQ ID NO: 27.

11. The aptamer of claim 10, wherein 5W has the nucleotide sequence of SEQ ID NO: 26, 3W has the nucleotide sequence of SEQ ID NO: 28 and/or C has the nucleotide sequence of SEQ ID NO: 24.

12. The aptamer of claim 1 having the nucleotide sequence of SEQ ID NO: 1, SEQ ID NO: 6, SEQ ID NO: 8, SEQ ID NO: 9, SEQ ID NO: 10, SEQ ID NO: 11 or SEQ ID NO: 13.

13. A method for detecting Factor XIa in a sample, the method comprising:
  (i) contacting the aptamer of claim 1 with the sample;
  (ii) determining the presence or the absence of a complex between Factor XIa and the aptamer; and
  (iii) detecting Factor XIa in the sample if the complex of step (ii) is determined to be present.

14. The method of claim 13, further comprising, when the complex of step (ii) is determined to be present, (iv) quantifying the amount of Factor XIa in the sample based on the amount of the complex.

* * * * *

SEQUENCE LISTING

<160> NUMBER OF SEQ ID NOS: 69

<210> SEQ ID NO 1
<211> LENGTH: 74
<212> TYPE: DNA
<213> ORGANISM: Artificial Sequence
<220> FEATURE:
<223> OTHER INFORMATION: FELLIAP aptamer

<400> SEQUENCE: 1

```
gaattctaat acgactcact ataaacctat cggactattg ttagtgattt ttatagtgtg      60
cgtccaacac atcg                                                       74
```

<210> SEQ ID NO 2
<211> LENGTH: 77
<212> TYPE: DNA
<213> ORGANISM: Artificial Sequence
<220> FEATURE:
<223> OTHER INFORMATION: NRMAPT1 aptamer

<400> SEQUENCE: 2

```
gaattctaat acgactcact atatacgtgg ttctttttttt agggagttcg atcctgaggc     60
ctgcgtccaa cacatcg                                                    77
```

<210> SEQ ID NO 3
<211> LENGTH: 78
<212> TYPE: DNA
<213> ORGANISM: Artificial Sequence
<220> FEATURE:
<223> OTHER INFORMATION: APT10_E aptamer

<400> SEQUENCE: 3

```
gaattctaat acgactcact atatgtcact ctgatcaaaa attttgtagt catcttgtta      60
tgcgcgtcca acacatcg                                                   78
```

<210> SEQ ID NO 4
<211> LENGTH: 78
<212> TYPE: DNA
<213> ORGANISM: Artificial Sequence
<220> FEATURE:
<223> OTHER INFORMATION: NRMAPT3 aptamer

<400> SEQUENCE: 4

```
gaattctaat acgactcact atacataaaa actatatacg tggttctttt tttagttttt      60
cgtgcgtcca acacatcg                                                   78
```

<210> SEQ ID NO 5
<211> LENGTH: 78
<212> TYPE: DNA
<213> ORGANISM: Artificial Sequence
<220> FEATURE:
<223> OTHER INFORMATION: NRMAPT4 aptamer

<400> SEQUENCE: 5

```
gaattctaat acgactcact atatcttaca tggccccatt attttagagt tcattccgat      60
tgggcgtcca acacatcg                                                   78
```

<210> SEQ ID NO 6
<211> LENGTH: 73
<212> TYPE: DNA
<213> ORGANISM: Artificial Sequence
<220> FEATURE:
<223> OTHER INFORMATION: APT10_D aptamer

```
<400> SEQUENCE: 6
gaattctaat acgactcact ataaacctat cggactattg ttagtgattt ttagagtggc    60
gtccaacaca tcg                                                      73

<210> SEQ ID NO 7
<211> LENGTH: 78
<212> TYPE: DNA
<213> ORGANISM: Artificial Sequence
<220> FEATURE:
<223> OTHER INFORMATION: NRMAPT6 aptamer

<400> SEQUENCE: 7
gaattctaat acgactcact atagcgtata cgtggttctt ttttcgcagg atagtatgta    60
tttgcgtcca acacatcg                                                 78

<210> SEQ ID NO 8
<211> LENGTH: 74
<212> TYPE: DNA
<213> ORGANISM: Artificial Sequence
<220> FEATURE:
<223> OTHER INFORMATION: NRMAPT7 aptamer

<400> SEQUENCE: 8
gaattctaat acgactcact ataaacctat cgtactattg ttagtgattt ttatagtgtg    60
cgtccaacac atcg                                                     74

<210> SEQ ID NO 9
<211> LENGTH: 74
<212> TYPE: DNA
<213> ORGANISM: Artificial Sequence
<220> FEATURE:
<223> OTHER INFORMATION: APT10_A aptamer

<400> SEQUENCE: 9
gaattctaat acgactcact ataaacctat cggactattg ttagtgattt ttatagtttg    60
cgtccaacac atcg                                                     74

<210> SEQ ID NO 10
<211> LENGTH: 74
<212> TYPE: DNA
<213> ORGANISM: Artificial Sequence
<220> FEATURE:
<223> OTHER INFORMATION: NRMAPT9 aptamer

<400> SEQUENCE: 10
gaattctaat acgactcact ataaacctat ctgactattg ttagtgattt ttatagtgtg    60
cgtccaacac atcg                                                     74

<210> SEQ ID NO 11
<211> LENGTH: 74
<212> TYPE: DNA
<213> ORGANISM: Artificial Sequence
<220> FEATURE:
<223> OTHER INFORMATION: NRMAPT10 aptamer

<400> SEQUENCE: 11
gaattctaat acgactcact ataaacctat cggactattg ttattgattt ttatagtgtg    60
cgtccaacac atcg                                                     74

<210> SEQ ID NO 12
```

```
<211> LENGTH: 78
<212> TYPE: DNA
<213> ORGANISM: Artificial Sequence
<220> FEATURE:
<223> OTHER INFORMATION: NRMAPT11 aptamer

<400> SEQUENCE: 12
gaattctaat acgactcact atacataaaa actatatacg tggttctttt tttagttttt    60
cttgcgtcca acacatcg                                                  78

<210> SEQ ID NO 13
<211> LENGTH: 74
<212> TYPE: DNA
<213> ORGANISM: Artificial Sequence
<220> FEATURE:
<223> OTHER INFORMATION: APT10_B aptamer

<400> SEQUENCE: 13
gaattctaat acgactcact ataaacctat cggactattg ttagtgattt ttatattgtg    60
cgtccaacac atcg                                                      74

<210> SEQ ID NO 14
<211> LENGTH: 74
<212> TYPE: DNA
<213> ORGANISM: Artificial Sequence
<220> FEATURE:
<223> OTHER INFORMATION: APT10_C aptamer

<400> SEQUENCE: 14
gaattctaat acgactcact ataaacctat cggactattt ttagtgattt ttatagtgtg    60
cgtccaacac atcg                                                      74

<210> SEQ ID NO 15
<211> LENGTH: 74
<212> TYPE: DNA
<213> ORGANISM: Artificial Sequence
<220> FEATURE:
<223> OTHER INFORMATION: NRMAPT14

<400> SEQUENCE: 15
gaattctaat acgactcact ataaacctat tggactattg ttagtgattt ttatagtgtg    60
cgtccaacac atcg                                                      74

<210> SEQ ID NO 16
<211> LENGTH: 77
<212> TYPE: DNA
<213> ORGANISM: Artificial Sequence
<220> FEATURE:
<223> OTHER INFORMATION: NRMAPT15 aptamer

<400> SEQUENCE: 16
gaattctaat acgactcact atacacgtgg ttctttattt agttatgtcg tcgtttttc     60 atgcgtccaa cacatcg                                                   77

<210> SEQ ID NO 17
<211> LENGTH: 74
<212> TYPE: DNA
<213> ORGANISM: Artificial Sequence
<220> FEATURE:
<223> OTHER INFORMATION: NRMAPT16 aptamer

<400> SEQUENCE: 17
gaattctaat acgactcact ataaacctat cggactattg ttagttattt ttatagtgtg    60
```
cgtccaacac atcg                                                          74

<210> SEQ ID NO 18
<211> LENGTH: 74
<212> TYPE: DNA
<213> ORGANISM: Artificial Sequence
<220> FEATURE:
<223> OTHER INFORMATION: NRMAPT17 aptamer

<400> SEQUENCE: 18
gaattctaat acgactcact ataaacctat cggactattg tcagtgattt ttatagtgtg        60
cgtccaacac atcg                                                          74

<210> SEQ ID NO 19
<211> LENGTH: 78
<212> TYPE: DNA
<213> ORGANISM: Artificial Sequence
<220> FEATURE:
<223> OTHER INFORMATION: NRMAPT18 aptamer

<400> SEQUENCE: 19
gaattctaat acgactcact atacataaaa actatatact tggttctttt tttagtttt         60 cgtgcgtcca acacatcg                                                      78

<210> SEQ ID NO 20
<211> LENGTH: 78
<212> TYPE: DNA
<213> ORGANISM: Artificial Sequence
<220> FEATURE:
<223> OTHER INFORMATION: NRMAPT19 aptamer

<400> SEQUENCE: 20
gaattctaat acgactcact atacacaaaa actatatacc tggttctttt tttagtttt         60 cgtgcgtcca acacatcg                                                      78

<210> SEQ ID NO 21
<211> LENGTH: 78
<212> TYPE: DNA
<213> ORGANISM: Artificial Sequence
<220> FEATURE:
<223> OTHER INFORMATION: NRMAPT20 aptamer

<400> SEQUENCE: 21
gaattctaat acgactcact ataaacacac aaacctattt ttcgattttc ctgccatcac        60
tccgcgtcca acacatcg                                                      78

<210> SEQ ID NO 22
<211> LENGTH: 78
<212> TYPE: DNA
<213> ORGANISM: Artificial Sequence
<220> FEATURE:
<223> OTHER INFORMATION: NRMAPT21

<400> SEQUENCE: 22
gaattctaat acgactcact atacataaaa actatatacg ttgttctttt tttagtttt         60 cgtgcgtcca acacatcg                                                      78

<210> SEQ ID NO 23
<211> LENGTH: 36
<212> TYPE: DNA
<213> ORGANISM: Artificial Sequence
<220> FEATURE:

```
<223> OTHER INFORMATION: Core consensus sequence (IIa)
<220> FEATURE:
<221> NAME/KEY: variation
<222> LOCATION: (8)..(8)
<223> OTHER INFORMATION: n is a, t/u, c or g
<220> FEATURE:
<221> NAME/KEY: misc_feature
<222> LOCATION: (8)..(10)
<223> OTHER INFORMATION: n is a, c, g, t or u
<220> FEATURE:
<221> NAME/KEY: variation
<222> LOCATION: (9)..(9)
<223> OTHER INFORMATION: n is a, t/u, c or g
<220> FEATURE:
<221> NAME/KEY: variation
<222> LOCATION: (10)..(10)
<223> OTHER INFORMATION: n is a, t/u, c or g
<220> FEATURE:
<221> NAME/KEY: variation
<222> LOCATION: (21)..(21)
<223> OTHER INFORMATION: n is a, t/u, c or g
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: variation
<222> LOCATION: (23)..(23)
<223> OTHER INFORMATION: n is a, t/u, c or g
<220> FEATURE:
<221> NAME/KEY: misc_feature
<222> LOCATION: (23)..(23)
<223> OTHER INFORMATION: n is a, c, g, t or u
<220> FEATURE:
<221> NAME/KEY: variation
<222> LOCATION: (31)..(31)
<223> OTHER INFORMATION: n is a, t/u, c or g
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: variation
<222> LOCATION: (33)..(33)
<223> OTHER INFORMATION: n is a, t/u, c or g
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: variation
<222> LOCATION: (35)..(35)
<223> OTHER INFORMATION: n is a, t/u, c or g
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: variation
<222> LOCATION: (36)..(36)
<223> OTHER INFORMATION: n is absent or is a, t/u, c or g

<400> SEQUENCE: 23
aacctatnnn actattvtda ntnatttta nantnn                           36

<210> SEQ ID NO 24
<211> LENGTH: 36
<212> TYPE: DNA
<213> ORGANISM: Artificial Sequence
<220> FEATURE:
<223> OTHER INFORMATION: Core region of the FELIAP aptamer

<400> SEQUENCE: 24
aacctatcgg actattgtta gtgattttta tagtgt                          36
```

```
<210> SEQ ID NO 25
<211> LENGTH: 23
<212> TYPE: DNA
<213> ORGANISM: Artificial Sequence
<220> FEATURE:
<223> OTHER INFORMATION: 5W consensus sequence (IIIa)
<220> FEATURE:
<221> NAME/KEY: variation
<222> LOCATION: (1)..(17)
<223> OTHER INFORMATION: n is a, t/u, c or g
<220> FEATURE:
<221> NAME/KEY: misc_feature
<222> LOCATION: (1)..(17)
<223> OTHER INFORMATION: n is a, c, g, t or u
<220> FEATURE:
<221> NAME/KEY: variation
<222> LOCATION: (19)..(19)
<223> OTHER INFORMATION: n is a, t/u, c or g
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: variation
<222> LOCATION: (21)..(21)
<223> OTHER INFORMATION: n is a, t/u, c or g
<220> FEATURE:
<221> NAME/KEY: misc_feature
<222> LOCATION: (21)..(21)
<223> OTHER INFORMATION: n is a, c, g, t or u

<400> SEQUENCE: 25
nnnnnnnnnn nnnnnnnant nta                                      23

<210> SEQ ID NO 26
<211> LENGTH: 23
<212> TYPE: DNA
<213> ORGANISM: Artificial Sequence
<220> FEATURE:
<223> OTHER INFORMATION: 5' wing of the aptamers of the Example

<400> SEQUENCE: 26
gaattctaat acgactcact ata                                      23

<210> SEQ ID NO 27
<211> LENGTH: 15
<212> TYPE: DNA
<213> ORGANISM: Artificial Sequence
<220> FEATURE:
<223> OTHER INFORMATION: 3W consensus sequence (VIa)
<220> FEATURE:
<221> NAME/KEY: variation
<222> LOCATION: (1)..(15)
<223> OTHER INFORMATION: n = a, t/u, c or g
<220> FEATURE:
<221> NAME/KEY: misc_feature
<222> LOCATION: (1)..(15)
<223> OTHER INFORMATION: n is a, c, g, t or u

<400> SEQUENCE: 27
nnnnnnnnnn nnnnn                                               15

<210> SEQ ID NO 28
<211> LENGTH: 15
<212> TYPE: DNA
<213> ORGANISM: Artificial Sequence
<220> FEATURE:
<223> OTHER INFORMATION: 3' wing of the aptamers of the Example

<400> SEQUENCE: 28
gcgtccaaca catcg                                               15
```

<210> SEQ ID NO 29
<211> LENGTH: 78
<212> TYPE: DNA
<213> ORGANISM: Artificial Sequence
<220> FEATURE:
<223> OTHER INFORMATION: Aptamers of the library of the Examples
<220> FEATURE:
<221> NAME/KEY: variation
<222> LOCATION: (24)..(64)
<223> OTHER INFORMATION: n is a, t, c or g
<220> FEATURE:
<221> NAME/KEY: misc_feature
<222> LOCATION: (24)..(63)
<223> OTHER INFORMATION: n is a, c, g, or t

<400> SEQUENCE: 29
gaattctaat acgactcact atannnnnnn nnnnnnnnnn nnnnnnnnnn nnnnnnnnn    60 nnngcgtcca acacatcg    78

<210> SEQ ID NO 30
<211> LENGTH: 35
<212> TYPE: DNA
<213> ORGANISM: Artificial Sequence
<220> FEATURE:
<223> OTHER INFORMATION: Core of the APT10_A aptamer

<400> SEQUENCE: 30
aacctatcgg actattgtta gtgattttta gagtg    35

<210> SEQ ID NO 31
<211> LENGTH: 36
<212> TYPE: DNA
<213> ORGANISM: Artificial Sequence
<220> FEATURE:
<223> OTHER INFORMATION: Core of the NRMAPT7 aptamer

<400> SEQUENCE: 31
aacctatcgt actattgtta gtgattttta tagtgt    36

<210> SEQ ID NO 32
<211> LENGTH: 36
<212> TYPE: DNA
<213> ORGANISM: Artificial Sequence
<220> FEATURE:
<223> OTHER INFORMATION: Core of the APT10_A aptamer

<400> SEQUENCE: 32
aacctatcgg actattgtta gtgattttta tagttt    36

<210> SEQ ID NO 33
<211> LENGTH: 36
<212> TYPE: DNA
<213> ORGANISM: Artificial Sequence
<220> FEATURE:
<223> OTHER INFORMATION: Core of the NRMAPT9 aptamer

<400> SEQUENCE: 33
aacctatctg actattgtta gtgatttttta tagtgt    36

<210> SEQ ID NO 34
<211> LENGTH: 36
<212> TYPE: DNA
<213> ORGANISM: Artificial Sequence
<220> FEATURE:
<223> OTHER INFORMATION: Core of the NRMAPT10 aptamer

<400> SEQUENCE: 34
aacctatcgg actattgtta ttgattttta tagtgt        36

<210> SEQ ID NO 35
<211> LENGTH: 36
<212> TYPE: DNA
<213> ORGANISM: Artificial Sequence
<220> FEATURE:
<223> OTHER INFORMATION: Core of the APT10_B aptamer

<400> SEQUENCE: 35
aacctatcgg actattgtta gtgattttta tattgt        36

<210> SEQ ID NO 36
<211> LENGTH: 36
<212> TYPE: DNA
<213> ORGANISM: Artificial Sequence
<220> FEATURE:
<223> OTHER INFORMATION: Core of the APT10_C aptamer

<400> SEQUENCE: 36
aacctatcgg actatttta gtgattttta tagtgt         36

<210> SEQ ID NO 37
<211> LENGTH: 36
<212> TYPE: DNA
<213> ORGANISM: Artificial Sequence
<220> FEATURE:
<223> OTHER INFORMATION: Core of the NRMAPT14 aptamer

<400> SEQUENCE: 37
aacctattgg actattgtta gtgattttta tagtgt        36

<210> SEQ ID NO 38
<211> LENGTH: 36
<212> TYPE: DNA
<213> ORGANISM: Artificial Sequence
<220> FEATURE:
<223> OTHER INFORMATION: Core of the NRMAPT16 aptamer

<400> SEQUENCE: 38
aacctatcgg actattgtta gttattttta tagtgt        36

<210> SEQ ID NO 39
<211> LENGTH: 36
<212> TYPE: DNA
<213> ORGANISM: Artificial Sequence
<220> FEATURE:
<223> OTHER INFORMATION: Core of the NRMAPT17 aptamer

<400> SEQUENCE: 39
aacctatcgg actattgtca gtgattttta tagtgt        36

<210> SEQ ID NO 40
<211> LENGTH: 23
<212> TYPE: DNA
<213> ORGANISM: Artificial Sequence
<220> FEATURE:
<223> OTHER INFORMATION: Forward primer (A)

<400> SEQUENCE: 40
gaattctaat acgactcact ata                     23

<210> SEQ ID NO 41
<211> LENGTH: 15
<212> TYPE: DNA

```
<213> ORGANISM: Artificial Sequence
<220> FEATURE:
<223> OTHER INFORMATION: Reverse primer (B)

<400> SEQUENCE: 41
gcgtccaaca catcg                                                        15

<210> SEQ ID NO 42
<211> LENGTH: 97
<212> TYPE: DNA
<213> ORGANISM: Artificial Sequence
<220> FEATURE:
<223> OTHER INFORMATION: Forward primer HTS
<220> FEATURE:
<221> NAME/KEY: variation
<222> LOCATION: (71)..(74)
<223> OTHER INFORMATION: n is a, t, c or g
<220> FEATURE:
<221> NAME/KEY: misc_feature
<222> LOCATION: (71)..(74)
<223> OTHER INFORMATION: n is a, c, g, or t

<400> SEQUENCE: 42
aatgatacgg cgaccaccga gatctacact agatcgcaca ctctttccct acacgacgct      60
cttccgatct nnnngaattc taatacgact cactata                               97

<210> SEQ ID NO 43
<211> LENGTH: 162
<212> TYPE: DNA
<213> ORGANISM: Artificial Sequence
<220> FEATURE:
<223> OTHER INFORMATION: Reverse primer HTS

<400> SEQUENCE: 43
caagcagaag acggcatacg agattcgcct tagtgactgg agttcagacg tgtgctcttc      60
cgatctcgat gtgttggaca agcagaagac ggcatacgag attcgcctta gtgactggag    120
ttcagacgtg tgctcttccg atctcgatgt gttggacgcc gc                        162

<210> SEQ ID NO 44
<211> LENGTH: 74
<212> TYPE: DNA
<213> ORGANISM: Artificial Sequence
<220> FEATURE:
<223> OTHER INFORMATION: SCRAPT control aptamer

<400> SEQUENCE: 44
gaattctaat acgactcact ataaacctat cggactattg ttagtgattt ttatagtgtg      60
cgtccaacac atcg                                                       74

<210> SEQ ID NO 45
<211> LENGTH: 22
<212> TYPE: DNA
<213> ORGANISM: Artificial Sequence
<220> FEATURE:
<223> OTHER INFORMATION: Core of Apt4-1 aptamer

<400> SEQUENCE: 45
gcgtccaaca catcgtattc at                                              22

<210> SEQ ID NO 46
<211> LENGTH: 40
<212> TYPE: DNA
<213> ORGANISM: Artificial Sequence
<220> FEATURE:
<223> OTHER INFORMATION: Core of Apt4-2 aptamer
```

<400> SEQUENCE: 46
tgggatggcg tgggagggct gtagggagcg ttcagtgggt         40

<210> SEQ ID NO 47
<211> LENGTH: 40
<212> TYPE: DNA
<213> ORGANISM: Artificial Sequence
<220> FEATURE:
<223> OTHER INFORMATION: Core of Apt4-3 aptamer

<400> SEQUENCE: 47
gggagggcgt ggatggctgg tgtgaggtct tgtgtttgtt         40

<210> SEQ ID NO 48
<211> LENGTH: 17
<212> TYPE: DNA
<213> ORGANISM: Artificial Sequence
<220> FEATURE:
<223> OTHER INFORMATION: Core of Apt4-4 aptamer

<400> SEQUENCE: 48
gggagcgttc agtgggt                                  17

<210> SEQ ID NO 49
<211> LENGTH: 23
<212> TYPE: DNA
<213> ORGANISM: Artificial Sequence
<220> FEATURE:
<223> OTHER INFORMATION: Core of Apt4-5 aptamer

<400> SEQUENCE: 49
gcgtccaaca catcggatga tat                           23

<210> SEQ ID NO 50
<211> LENGTH: 23
<212> TYPE: DNA
<213> ORGANISM: Artificial Sequence
<220> FEATURE:
<223> OTHER INFORMATION: Core of Apt4-6 aptamer

<400> SEQUENCE: 50
tgcgtccaac acatcgtatt cat                           23

<210> SEQ ID NO 51
<211> LENGTH: 40
<212> TYPE: DNA
<213> ORGANISM: Artificial Sequence
<220> FEATURE:
<223> OTHER INFORMATION: Core of Apt4-7 aptamer

<400> SEQUENCE: 51
tgggatggcg tgggagggct gtagtgagcg ttcagtgggt         40

<210> SEQ ID NO 52
<211> LENGTH: 21
<212> TYPE: DNA
<213> ORGANISM: Artificial Sequence
<220> FEATURE:
<223> OTHER INFORMATION: Core of Apt4-8 aptamer

<400> SEQUENCE: 52
cgtccaacac atcgtattca t                             21

<210> SEQ ID NO 53

```
<211> LENGTH: 22
<212> TYPE: DNA
<213> ORGANISM: Artificial Sequence
<220> FEATURE:
<223> OTHER INFORMATION: Core of Apt4-9 aptamer

<400> SEQUENCE: 53
cttgcccact atcgacttca cc                                              22

<210> SEQ ID NO 54
<211> LENGTH: 21
<212> TYPE: DNA
<213> ORGANISM: Artificial Sequence
<220> FEATURE:
<223> OTHER INFORMATION: Core of Apt4-10 aptamer

<400> SEQUENCE: 54
gcgtccaaca catcgtaagt a                                               21

<210> SEQ ID NO 55
<211> LENGTH: 26
<212> TYPE: DNA
<213> ORGANISM: Artificial Sequence
<220> FEATURE:
<223> OTHER INFORMATION: Core of Apt10-2 aptamer

<400> SEQUENCE: 55
cactgcgtcc aacacatcgt attcat                                          26

<210> SEQ ID NO 56
<211> LENGTH: 40
<212> TYPE: DNA
<213> ORGANISM: Artificial Sequence
<220> FEATURE:
<223> OTHER INFORMATION: Core of Apt10-5 aptamer

<400> SEQUENCE: 56
gggagggcgt ggatggctgt tgtgaggtct tgtgtttgtt                           40

<210> SEQ ID NO 57
<211> LENGTH: 40
<212> TYPE: DNA
<213> ORGANISM: Artificial Sequence
<220> FEATURE:
<223> OTHER INFORMATION: Core of Apt10-6 aptamer

<400> SEQUENCE: 57
tgggatggcg tgggagggct gtagggagcg tttagtgggt                           40

<210> SEQ ID NO 58
<211> LENGTH: 40
<212> TYPE: DNA
<213> ORGANISM: Artificial Sequence
<220> FEATURE:
<223> OTHER INFORMATION: Core of Apt10-7 aptamer

<400> SEQUENCE: 58
tgggatggcg tgggagggct gtagtgagcg ttcattgggt                           40

<210> SEQ ID NO 59
<211> LENGTH: 40
<212> TYPE: DNA
<213> ORGANISM: Artificial Sequence
<220> FEATURE:
<223> OTHER INFORMATION: Core of Apt10-9 aptamer

<400> SEQUENCE: 59
```

```
tgggatggcg tgggagggct gtagtgagcg tttagtgggt                          40

<210> SEQ ID NO 60
<211> LENGTH: 65
<212> TYPE: DNA
<213> ORGANISM: Artificial Sequence
<220> FEATURE:
<223> OTHER INFORMATION: FELIAP_64 aptamer

<400> SEQUENCE: 60
ctaatacgac tcactataaa cctatcggac tattgttagt gattttata gtgtgcgtcc    60 aacac                                                               65

<210> SEQ ID NO 61
<211> LENGTH: 55
<212> TYPE: DNA
<213> ORGANISM: Artificial Sequence
<220> FEATURE:
<223> OTHER INFORMATION: FELIAP_55 aptamer

<400> SEQUENCE: 61
tacgactcac tataaaccta tcggactatt gttagtgatt tttatagtgt gcgtc         55

<210> SEQ ID NO 62
<211> LENGTH: 49
<212> TYPE: DNA
<213> ORGANISM: Artificial Sequence
<220> FEATURE:
<223> OTHER INFORMATION: FELIAP_49 aptamer

<400> SEQUENCE: 62
gactcactat aaacctatcg gactattgtt agtgattttt atagtgtgc                49

<210> SEQ ID NO 63
<211> LENGTH: 42
<212> TYPE: DNA
<213> ORGANISM: Artificial Sequence
<220> FEATURE:
<223> OTHER INFORMATION: FELIAP_42 aptamer

<400> SEQUENCE: 63
cactataaac ctatcggact attgttagtg attttttatag tg                     42

<210> SEQ ID NO 64
<211> LENGTH: 38
<212> TYPE: DNA
<213> ORGANISM: Artificial Sequence
<220> FEATURE:
<223> OTHER INFORMATION: FELIAP_38 aptamer

<400> SEQUENCE: 64
ctataaacct atcggactat tgttagtgat ttttatag                           38

<210> SEQ ID NO 65
<211> LENGTH: 32
<212> TYPE: DNA
<213> ORGANISM: Artificial Sequence
<220> FEATURE:
<223> OTHER INFORMATION: FELIAP_32 aptamer

<400> SEQUENCE: 65
taaacctatc ggactattgt tagtgatttt ta                                 32

<210> SEQ ID NO 66
```

```
<211> LENGTH: 18
<212> TYPE: DNA
<213> ORGANISM: Artificial Sequence
<220> FEATURE:
<223> OTHER INFORMATION: 5W consensus sequence (IIIb)
<220> FEATURE:
<221> NAME/KEY: variation
<222> LOCATION: (1)..(12)
<223> OTHER INFORMATION: n is present or absent and can be a, t/u, c or
      g
<220> FEATURE:
<221> NAME/KEY: misc_feature
<222> LOCATION: (1)..(12)
<223> OTHER INFORMATION: n is a, c, g, t or u
<220> FEATURE:
<221> NAME/KEY: variation
<222> LOCATION: (14)..(14)
<223> OTHER INFORMATION: n is present or absent and can be a, t/u, c or
      g
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: variation
<222> LOCATION: (16)..(16)
<223> OTHER INFORMATION: n is present or absent and can be a, t/u, c or
      g
<220> FEATURE:
<221> NAME/KEY: misc_feature
<222> LOCATION: (16)..(16)
<223> OTHER INFORMATION: n is a, c, g, t or u

<400> SEQUENCE: 66
nnnnnnnnnn nnantnta                                                 18

<210> SEQ ID NO 67
<211> LENGTH: 11
<212> TYPE: DNA
<213> ORGANISM: Artificial Sequence
<220> FEATURE:
<223> OTHER INFORMATION: 3W consensus sequence (IVb)
<220> FEATURE:
<221> NAME/KEY: variation
<222> LOCATION: (1)..(11)
<223> OTHER INFORMATION: n is absent or present and can be a, t/u, c or
      g
<220> FEATURE:
<221> NAME/KEY: misc_feature
<222> LOCATION: (1)..(11)
<223> OTHER INFORMATION: n is a, c, g, t or u

<400> SEQUENCE: 67
nnnnnnnnnn n                                                        11

<210> SEQ ID NO 68
<211> LENGTH: 33
<212> TYPE: DNA
<213> ORGANISM: Artificial Sequence
<220> FEATURE:
<223> OTHER INFORMATION: Core consensus sequence (IIb)
<220> FEATURE:
<221> NAME/KEY: variation
<222> LOCATION: (8)..(10)
<223> OTHER INFORMATION: n is a, t/u, c or g
<220> FEATURE:
<221> NAME/KEY: misc_feature
<222> LOCATION: (8)..(10)
<223> OTHER INFORMATION: n is a, c, g, t or u
<220> FEATURE:
<221> NAME/KEY: variation
<222> LOCATION: (17)..(17)
<223> OTHER INFORMATION: n is a, t/u, c or g
<220> FEATURE:
<221> NAME/KEY: misc_feature
```

```
<222> LOCATION: (17)..(17)
<223> OTHER INFORMATION: n is a, c, g, t or u
<220> FEATURE:
<221> NAME/KEY: variation
<222> LOCATION: (19)..(19)
<223> OTHER INFORMATION: n is a, t/u, c or g
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: variation
<222> LOCATION: (21)..(21)
<223> OTHER INFORMATION: n is a, t/u, c or g
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: variation
<222> LOCATION: (23)..(23)
<223> OTHER INFORMATION: n is a, t/u, c or g
<220> FEATURE:
<221> NAME/KEY: misc_feature
<222> LOCATION: (23)..(23)
<223> OTHER INFORMATION: n is a, c, g, t or u
<220> FEATURE:
<221> NAME/KEY: variation
<222> LOCATION: (31)..(31)
<223> OTHER INFORMATION: n is a, t/u, c or g
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: variation
<222> LOCATION: (33)..(33)
<223> OTHER INFORMATION: n is a, t/u, c or g
<220> FEATURE:
<221> NAME/KEY: misc_feature
<222> LOCATION: (33)..(33)
<223> OTHER INFORMATION: n is a, c, g, t or u

<400> SEQUENCE: 68
aacctatnnn actattntna ntnattttta nan                                    33

<210> SEQ ID NO 69
<211> LENGTH: 40
<212> TYPE: DNA
<213> ORGANISM: Artificial Sequence
<220> FEATURE:
<223> OTHER INFORMATION: Core of APT10_E aptamer

<400> SEQUENCE: 69
tgtcactctg atcaaaaatt ttgtagtcat cttgttatgc                             40
```

UNITED STATES PATENT AND TRADEMARK OFFICE
CERTIFICATE OF CORRECTION

PATENT NO. : 10,494,634 B2  
APPLICATION NO. : 15/586581  
DATED : December 3, 2019  
INVENTOR(S) : William Peter Sheffield and David Apraku Donkor Page 1 of 1

It is certified that error appears in the above-identified patent and that said Letters Patent is hereby corrected as shown below:

In the Claims

In Claim 1, at Column 65, Line 61, before the following word "5W" insert -- - --.

In Claim 1, at Column 65, Line 66, before the following word "C" insert -- - --.

In Claim 1, at Column 66, Line 50, before the following word "3W" insert -- - --.

In Claim 1, at Column 66, Line 59, before the following word "the" insert -- - --.

In Claim 10, at Column 67, Line 23, before the following word "5W" insert -- - --.

In Claim 10, at Column 67, Line 30, before the following word "C" insert -- - --.

In Claim 10, at Column 67, Line 32, before the following word "3W" insert -- - --.

In Claim 10, at Column 68, Line 7, before the following word "the" insert -- - --.

In Claim 10, at Column 68, Line 11, before the following word "the" insert -- - --.

Signed and Sealed this  
Twenty-eighth Day of July, 2020

Andrei Iancu  
*Director of the United States Patent and Trademark Office*